(12) United States Patent
Isoaho et al.

(10) Patent No.: US 11,000,256 B2
(45) Date of Patent: May 11, 2021

(54) CALIBRATING AN X-RAY MEDICAL IMAGING DEVICE FOR CEPHALOMETRIC IMAGING

(71) Applicant: PaloDEx Group OY, Tuusula (FI)

(72) Inventors: Tero Isoaho, Tuusula (FI); Ilpo Saarela, Helsinki (FI); Esa Suuronen, Kerava (FI); Andreas Melin, Espoo (FI); Markku Ojala, Raisio (FI); Henri Setälä, Littoinen (FI)

(73) Assignee: PALODEX GROUP OY, Tuusula (FI)

( * ) Notice: Subject to any disclaimer, the term of this patent is extended or adjusted under 35 U.S.C. 154(b) by 0 days.

(21) Appl. No.: 16/185,670

(22) Filed: Nov. 9, 2018

(65) Prior Publication Data

US 2020/0146650 A1  May 14, 2020

(51) Int. Cl.
*A61B 6/00* (2006.01)
*A61B 6/04* (2006.01)
(Continued)

(52) U.S. Cl.
CPC .............. *A61B 6/584* (2013.01); *A61B 6/035* (2013.01); *A61B 6/04* (2013.01); *A61B 6/0407* (2013.01); *A61B 6/06* (2013.01); *A61B 6/14* (2013.01); *A61B 6/4007* (2013.01); *A61B 6/4021* (2013.01); *A61B 6/44* (2013.01); *A61B 6/4417* (2013.01); *A61B 6/4429* (2013.01); *A61B 6/4435* (2013.01); *A61B 6/4441* (2013.01);
(Continued)

(58) Field of Classification Search
CPC ....... A61B 6/0407; A61B 6/0457; A61B 6/06; A61B 6/14; A61B 6/4007; A61B 6/44; A61B 6/4417; A61B 6/4429; A61B 6/4435; A61B 6/4441; A61B 6/4452; A61B 6/501; A61B 6/54; A61B 6/547; A61B 6/58; A61B 6/582; A61B 6/583; A61B 6/584; A61B 6/588; A61B 6/589
USPC ............................ 378/38–40, 196, 197, 207
See application file for complete search history.

(56) References Cited

U.S. PATENT DOCUMENTS

| 5,058,147 A * | 10/1991 | Nishikawa | ............... A61B 6/14 378/38 |
| 6,169,780 B1 * | 1/2001 | Yoshimura | ............... A61B 6/14 378/38 |

(Continued)

FOREIGN PATENT DOCUMENTS

JP          2001346796 A     12/2001

*Primary Examiner* — Allen C. Ho
(74) *Attorney, Agent, or Firm* — Michael Best & Friedrich LLP

(57) ABSTRACT

Systems and methods for operating an imaging system to perform Cephalometric imaging. The imaging system includes a column, an upper shelf pivotably coupled to the column, a rotating part coupled to the upper shelf and linearly translatable along a length of the upper shelf in a direction radial to the column, a first x-ray source coupled to the rotating part, and an x-ray detector coupled to the rotating part on an opposite side of a first imaging volume from the first x-ray source. A center position of the Cephalometric patient support is determined relative to the imaging system in at least two dimensions by scanning the imaging volume while adjusting a pivot angle of the upper shelf and by scanning the imaging volume while adjusting a linear position of the rotating part along the upper shelf.

19 Claims, 13 Drawing Sheets

(51) Int. Cl.
*A61B 6/06* (2006.01)
*A61B 6/14* (2006.01)
*A61B 6/03* (2006.01)

(52) U.S. Cl.
CPC ............ *A61B 6/4452* (2013.01); *A61B 6/501* (2013.01); *A61B 6/54* (2013.01); *A61B 6/547* (2013.01); *A61B 6/58* (2013.01); *A61B 6/582* (2013.01); *A61B 6/588* (2013.01)

(56) References Cited

U.S. PATENT DOCUMENTS

| | | | | |
|---|---|---|---|---|
| 6,584,171 | B2* | 6/2003 | Suzuki | A61B 6/14 348/E3.023 |
| 7,016,461 | B2* | 3/2006 | Rotondo | A61B 6/14 378/39 |
| 7,092,483 | B2* | 8/2006 | Nyholm | A61B 6/06 378/38 |
| 7,103,141 | B2* | 9/2006 | Sonobe | A61B 6/14 378/108 |
| 7,197,109 | B2* | 3/2007 | Rotondo | A61B 6/14 378/196 |
| 7,269,242 | B2* | 9/2007 | Tanaka | A61B 6/0478 378/16 |
| 7,322,746 | B2* | 1/2008 | Beckhaus | A61B 6/032 378/19 |
| 7,424,091 | B2* | 9/2008 | Park | A61B 6/14 378/39 |
| 7,471,761 | B2* | 12/2008 | Michaeli | A61B 6/14 378/38 |
| 7,486,759 | B2* | 2/2009 | Suzuki | A61B 6/14 378/38 |
| 7,534,038 | B2* | 5/2009 | Rotondo | A61B 6/08 378/205 |
| 7,577,232 | B2* | 8/2009 | Tachibana | G03B 42/026 378/39 |
| 7,711,085 | B2* | 5/2010 | Suzuki | A61B 6/14 378/39 |
| 7,715,525 | B2* | 5/2010 | Spartiotis | A61B 6/14 378/38 |
| 7,798,708 | B2* | 9/2010 | Erhardt | A61B 6/032 250/370.09 |
| 7,804,933 | B2* | 9/2010 | Nyholm | A61B 6/14 378/39 |
| 7,961,841 | B2* | 6/2011 | Ro | A61B 6/4429 378/116 |
| 8,005,186 | B2* | 8/2011 | Lee | A61B 6/032 378/13 |
| 8,005,187 | B2* | 8/2011 | Suzuki | A61B 6/032 378/19 |
| 8,050,381 | B2* | 11/2011 | Mori | A61B 6/14 378/191 |
| 8,130,901 | B2* | 3/2012 | Müller | A61B 6/06 378/38 |
| 8,251,583 | B2* | 8/2012 | Cekov | A61B 6/14 378/191 |
| 8,300,762 | B2* | 10/2012 | Suzuki | A61B 6/032 378/39 |
| 8,363,919 | B2* | 1/2013 | Sebok | A61B 6/5264 382/131 |
| 8,588,364 | B2* | 11/2013 | Suzuki | A61B 6/14 378/38 |
| 8,861,679 | B2* | 10/2014 | Suuronen | A61B 6/00 378/98.5 |
| 8,979,364 | B2* | 3/2015 | Bothorel | A61B 6/4435 378/191 |
| 8,979,366 | B2* | 3/2015 | Tomoe | A61B 6/027 378/197 |
| 9,044,176 | B2* | 6/2015 | Loustauneau | A61B 6/06 |
| 9,259,196 | B2* | 2/2016 | Müller | A61B 6/14 |
| 9,265,466 | B2* | 2/2016 | Hirabayashi | A61B 6/0492 |
| 9,265,469 | B2* | 2/2016 | Baldini | A61B 6/4266 |
| 9,332,949 | B2* | 5/2016 | Lemaire | H01J 37/3045 |
| 9,532,753 | B2* | 1/2017 | Kim | A61B 6/032 |
| 9,538,966 | B2* | 1/2017 | Müller | A61B 6/405 |
| 9,538,968 | B2* | 1/2017 | Rotondo | A61B 6/032 |
| 9,592,020 | B2* | 3/2017 | Sandholm | A61B 6/5264 |
| 9,668,705 | B2* | 6/2017 | Yamakawa | A61B 6/14 |
| 9,888,891 | B2* | 2/2018 | Suuronen | A61B 6/4452 |
| 9,936,926 | B2* | 4/2018 | Eronen | A61B 6/06 |
| 9,962,131 | B2* | 5/2018 | Yoshikawa | A61B 6/4085 |
| 10,278,666 | B2* | 5/2019 | Eronen | A61B 6/032 |
| 10,335,108 | B2* | 7/2019 | Boll | A61B 6/032 |
| 10,376,231 | B2* | 8/2019 | Öjelund | A61B 6/542 |
| 10,405,815 | B2* | 9/2019 | Choi | G01T 1/161 |
| 10,405,816 | B2* | 9/2019 | Congy | A61B 6/06 |
| 10,420,525 | B2* | 9/2019 | Martino | A61B 6/14 |
| 10,485,495 | B2* | 11/2019 | Congy | A61B 6/0421 |
| 10,492,743 | B2* | 12/2019 | Kim | A61B 6/14 |
| 10,537,298 | B2* | 1/2020 | Martino | A61B 6/505 |
| 10,722,208 | B2* | 7/2020 | Antikainen | A61B 6/035 |
| 10,779,783 | B2* | 9/2020 | Ito | A61B 6/14 |
| 10,779,792 | B2* | 9/2020 | Arai | A61B 6/032 |
| 10,799,199 | B2* | 10/2020 | Vartiainen | A61B 6/4476 |
| 10,806,423 | B2* | 10/2020 | Sugihara | A61B 6/14 |
| 2007/0183567 | A1 | 8/2007 | Rotondo et al. | |
| 2017/0311915 | A1 | 11/2017 | Martino et al. | |

* cited by examiner

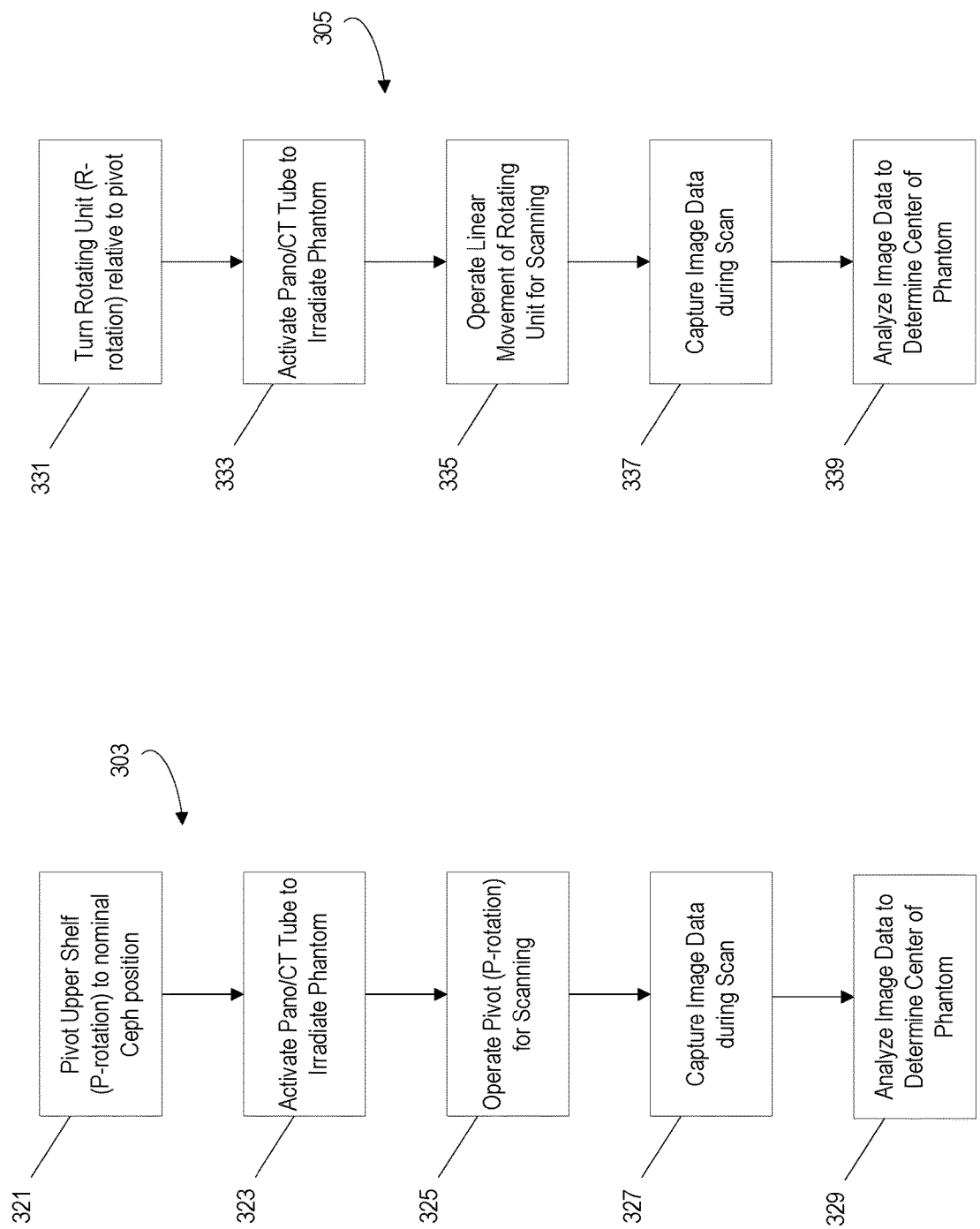

CALIBRATING AN X-RAY MEDICAL IMAGING DEVICE FOR CEPHALOMETRIC IMAGING

TECHNICAL FIELD

Embodiments relate generally to systems and methods for x-ray medical imaging.

BACKGROUND

Systems that utilize high energy radiation, for example X-ray radiation, to examine the internal structure of an object are known. These systems may be used to produce images of body parts. Detection systems, particularly those used in medical applications, direct X-rays through the body part of interest toward an X-ray detector. In certain kinds of X-ray imaging, the image is captured during a process in which the X-ray generator and the imaging device move around the patient's head according to a predetermined geometric path and speed profile. The movement of the X-ray generator and the imaging device is traditionally synchronized so that the imaging device surface is perpendicular to the layer-of-interest. In other kinds of X-ray imaging, the X-ray generator and the imaging device are aligned in a predetermined manner.

SUMMARY

One object of some embodiments is to provide a mechanism for calibrating an imaging system. For example, some embodiments provide a mechanism for calibrating the imaging system for use with a patient support by determining a position of the patient support relative to a known coordinate system of the x-ray imaging system. The techniques and systems described may be used in combination imaging systems, for example, a combination of Panoramic, Cephalometric, and/or Computed Tomography imaging modalities.

In one example, techniques and systems described help reduce drawbacks of Panoramic/Cephalometric/Computed Tomography (CT) combination imaging systems related to the calibration of critical components associated with the imaging systems. When, for example, an imaging system is modified or supplemented to allow for multiple types of images (for example, Panoramic, Cephalometric, and/or Computed Tomography (CT) images), the X-ray imaging system needs to be calibrated accurately in order to, for example, ensure accurate imaging and prevent multiple retakes of the images thereby preventing the patient from repeated X-rays and unnecessary exposure to X-ray radiation.

In some instances, Cephalometric imaging components are provided as an add-on or accessory to systems that are designed for Panoramic imaging. Systems and methods described herein provide for the calibration of an imaging system capable of capturing Panoramic, Cephalometric, and/or Computed Tomography (CT) images of the patient. In some, but not all, systems there is a first X-ray source used for Panoramic and Computed Tomography imaging and a second X-ray source used for Cephalometric imaging. Systems and methods described herein provide, among other things, for determining positions of add-on or accessory components relative to original or previously calibrated components of the imaging system by determining positions and/or orientations of one or more components relative to a coordinate frame of the imaging system.

In some instances, the x-ray imaging system includes a column, an upper shelf coupled to the column, and a rotating part coupled to the upper shelf. The x-ray imaging system is configured to controllably pivot the upper shelf relative to the column (e.g., a pivoting movement). Additionally, the x-ray imaging system is configured to controllably rotate the rotating part relative to the upper shelf and to provide a controllable linear movement of the rotating part along a length of the upper shelf in a direction radial to the column.

One embodiment includes an X-ray imaging system for medical imaging. The X-ray imaging unit includes a column. The X-ray imaging system also includes an upper shelf coupled to the column. The X-ray imaging system includes a rotating part rotatably coupled to the upper shelf and having a rotation axis with respect to the upper shelf. The rotating part includes an X-ray source. The rotating part or another component of the X-ray imaging system includes a source of visible light, for example, a laser, an LED, or other light source, and an X-ray imaging detector. The X-ray source and the X-ray imaging detector are configured to provide an image by means of at least a rotational movement (R) of the rotating part. The X-ray imaging system also includes a Cephalometric patient support configured to support a patient to be imaged. The Cephalometric patient support can be selectively attached to the column by a first arm, and includes a pair of adjustable ear rods, wherein each of the ear rods has an ear bud. The light source is configured to generate and project a beam of light to a fixed location on the X-ray imaging detector. In one example, the fixed location is associated with a Frankfurt plane of the patient. The Cephalometric patient support is adjustable to align the ear buds with the beam of light.

Some embodiments provide a method of operating an imaging system to perform Cephalometric imaging. The imaging system includes a column, an upper shelf coupled to the column, a rotating part coupled to the upper shelf and linearly translatable along a length of the upper shelf in a direction radial to the column, a first x-ray source coupled to the rotating part, and an x-ray detector coupled to the rotating part on an opposite side of a first imaging volume from the first x-ray source. At least one calibration sweep is performed by controllably adjusting a position of the x-ray detector relative to the Cephalometric patient support. Image data is captured by the x-ray detector while performing the at least one calibration sweep. A center position of the Cephalometric patient support is determined relative to the imaging system in at least two dimensions based on the image data captured while performing the at least one calibration sweep.

Another embodiment provides an imaging system that includes a column, an upper shelf coupled to the column, a rotating part coupled to the upper shelf and linearly translatable along a length of the upper shelf in a direction radial to the column, a first x-ray source coupled to the rotating part, an x-ray detector coupled to the rotating part on an opposite side of the first imaging volume from the first x-ray source, and a controller. The controller is configured to perform at least one calibration sweep by controllably adjusting a position of the x-ray detector relative to the Cephalometric patient support. Image data is captured by the x-ray detector while performing the at least one calibration sweep. The controller then determines a center position of the Cephalometric patient support relative to the imaging system in at least two dimension based on the image data captured while performing the at least one calibration sweep.

In some embodiments, the imaging system also includes a Cephalometric patient support arm that is selectively couplable to the column. The Cephalometric patient support is coupled to a distal end of the Cephalometric patient support arm and the imaging system determines an unknown position of the Cephalometric patient support and uses that determined position information to perform Cephalometric imaging.

In some embodiments, the imaging system also includes a Cephalometric x-ray source arm that is also selectively couplable to the column. A second x-ray source is coupled to the distal end of the Cephalometric x-ray source arm and further calibration is performed by the imaging system to determine a middle angle of the second x-ray source relative to the Cephalometric patient support. Cephalometric imaging is performed by emitting x-rays from the second x-ray source towards the Cephalometric patient support and capturing image data using the x-ray detector.

The term "medical imaging" refers to, for example, dental, extra-oral, oral, maxillofacial, carpus, or ears, nose, and throat imaging.

Further embodiments are defined in dependent claims. The features recited in dependent claims are mutually freely combinable unless otherwise explicitly stated.

The definitions of the below-defined verbs and terms shall be applied, unless a different definition is given in the claims or elsewhere in this description/specification.

The verb "comprise" is used in this document as an open limitation that neither excludes nor requires the existence of un-recited features. The verbs "include" and "have/has" are defined as in the same manner as the verb comprise.

The terms "a", "an" and "at least one", as used herein, are defined as one or more than one and the term "plurality" is defined as two or more than two. The term "another", as used herein, is defined as at least a second or more.

The term "or" is generally employed in its sense comprising "and/or" unless the content clearly dictates otherwise.

BRIEF DESCRIPTION OF THE DRAWINGS

FIG. 3B is a flow chart of one example of a pivot sweep calibration for use in the method of FIG. 3A.

FIG. 3C is a flow chart of one example of a linear sweep calibration for use in the method of FIG. 3A.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed.

Figure 1A:
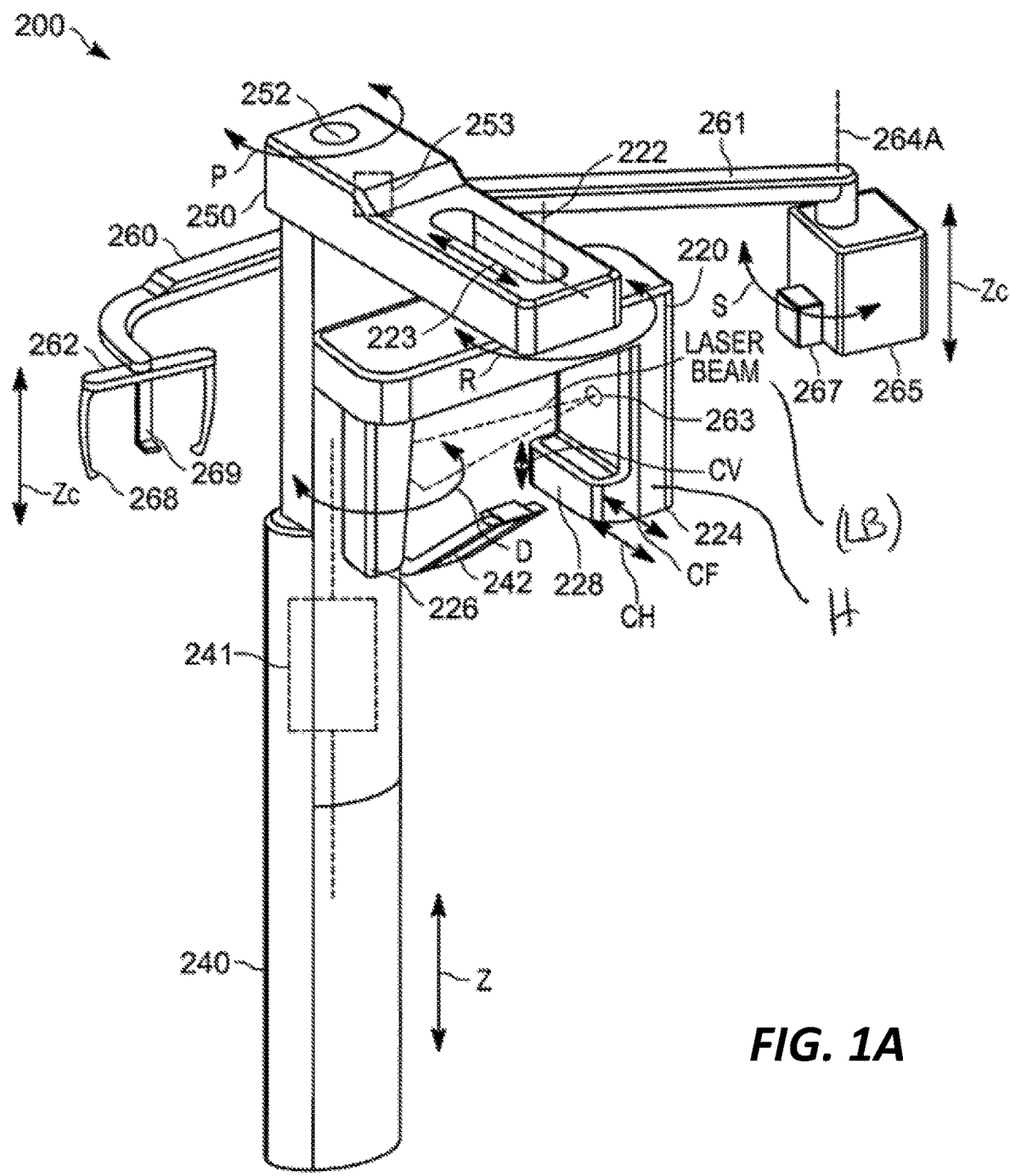
FIG. 1A illustrates an X-ray imaging system for a medical imaging and its main parts and movements.

FIG. 1A illustrates main parts of an X-ray imaging system 200, which can be used in medical imaging, for example, in extra-oral dental imaging.

The X-ray imaging system 200 includes a rotating part (gantry) 220, which includes a first X-ray source 224. An X-ray imaging detector unit 226 is also attached to the rotating part 220. As discussed in further detail below, the X-ray imaging detector unit 226 may include, for example, one or more x-ray detectors for capturing image data relating to x-rays emitted, for example, by the first X-ray source 224. In some implementations, a position of the X-ray imaging detector unit 226 is adjustable relative to the rotating part, for example, the X-ray imaging detector unit 226 is rotatable or movable in a linear fashion. In other examples, one or more individual x-ray detectors included in the X-ray imaging detector unit 226 may be moveable. The first X-ray source 224 and/or the X-ray imaging detector unit 226 provides, for example, a Panoramic, CT, or Cephalometric image by means of at least a rotational movement R (i.e., "R-movement") around a rotation axis 222 of the rotating part 220. The R-movement of the rotating part 220 is, for example, up to 400 degrees around the rotation axis 222. In the example illustrated, the first X-ray source 224 is positioned within a housing H. In some implementations, the housing H also includes a light source 263 (for example, a laser or LED) that can be utilized for determining alignment of various components.

The X-ray imaging system 200 also includes a second X-ray source 265 which may be attached to a column 240 by a second arm 261. The second X-ray source 265 includes an X-ray beam limiting device 267. Although described as two separate arms, the first arm 260 and the second arm 261 may be mechanically linked so as to operate in effect as a single arm. The single arm may be pivotally connected to the column 240 so that raising one end of the single arm causes the other end of the single arm to lower (for example, in a manner similar to a seesaw or teeter-totter).

The rotating part 220 includes a rotating motor, which is configured to rotate the rotating part 220 by means of rotation means (not shown). Alternatively, the rotating motor can be situated in an upper shelf 250 of the X-ray imaging system 200. In one example, the rotating part 220 is attached to the upper shelf 250.

The rotating part 220 has, for example, a form approximating a letter C and the first X-ray source 224 is on one end of the rotating part 220. The first X-ray source 224 may be common for two imaging modes—Panoramic imaging and CT imaging (e.g., CBCT imaging, where an X-ray beam is a cone-shaped beam). However, in some embodiments, the X-ray imaging system 200 might be configured to perform only one type of imaging (e.g., only CT imaging or only panoramic imaging) using the first X-ray source 224. In some CT imaging techniques, the X-ray beam is one of a pyramidal-shaped beam, half-moon-shaped cone beam, or other shaped beam.

In the example provided, the first X-ray source 224 also includes an X-ray beam limiting device 228 for the first X-ray source 224 and an X-ray beam limiting motor configured to adjust the X-ray beam limiting device 228, for example, in a horizontal direction (CH) and a vertical direction (CV). During imaging, the X-ray beam limiting device 228 controls the size and shape of the X-ray beam so that it matches the needs of a selected imaging protocol, a selected image size, and the related detector size.

Figure 1B:
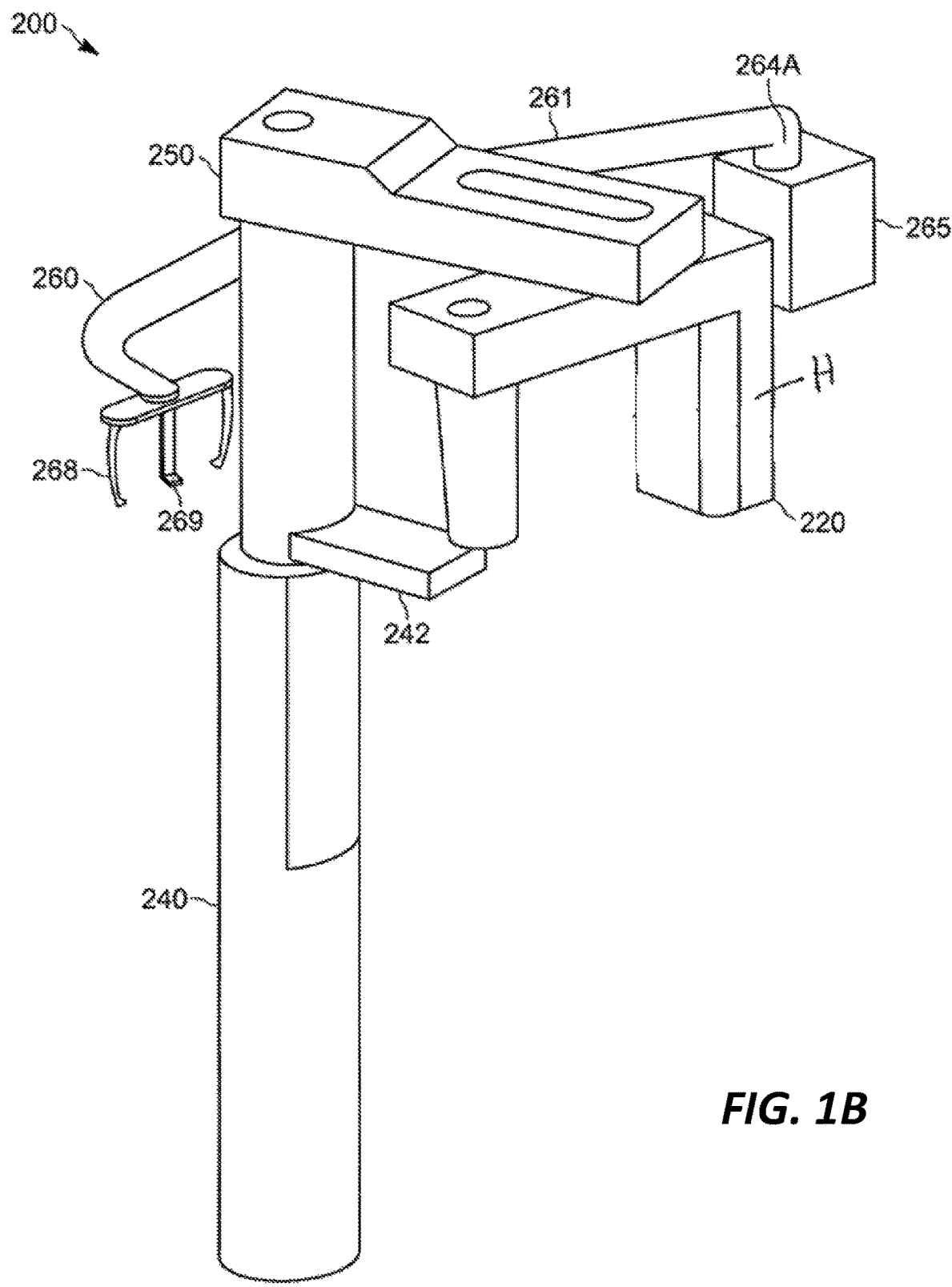
FIG. 1B illustrates the X-ray imaging system of FIG. 1A positioned for Panoramic/CT imaging.
Figure 1C:
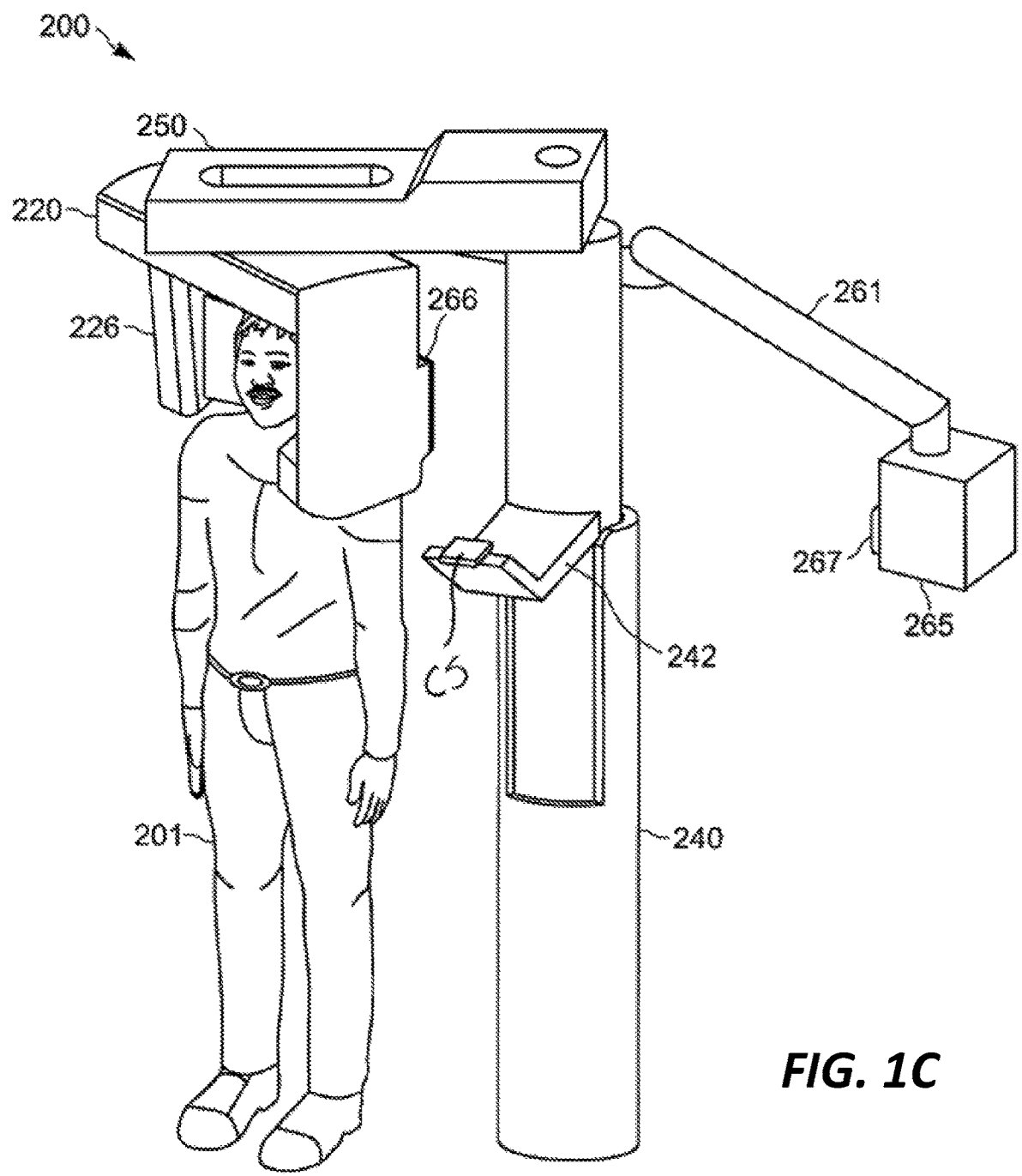
FIG. 1C illustrates the X-ray imaging system of FIG. 1A and a patient in a Cephalometric imaging position during an imaging.
Figure 1D:
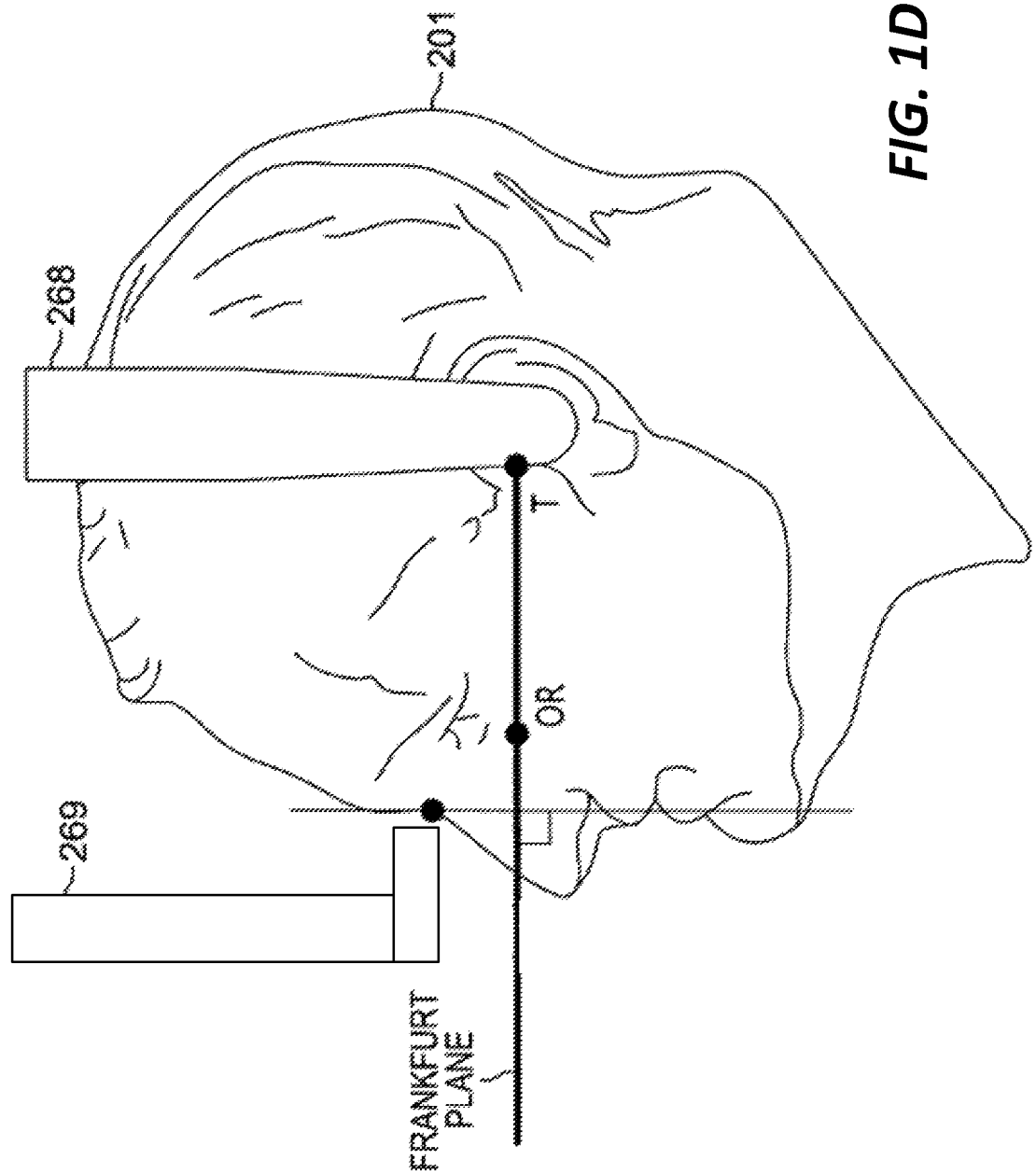
FIG. 1D is a side view of a patient positioned relative to a Cephalometric patient support during an imaging when in the Cephalometric imaging position of FIG. 1C.
Figure 1E:
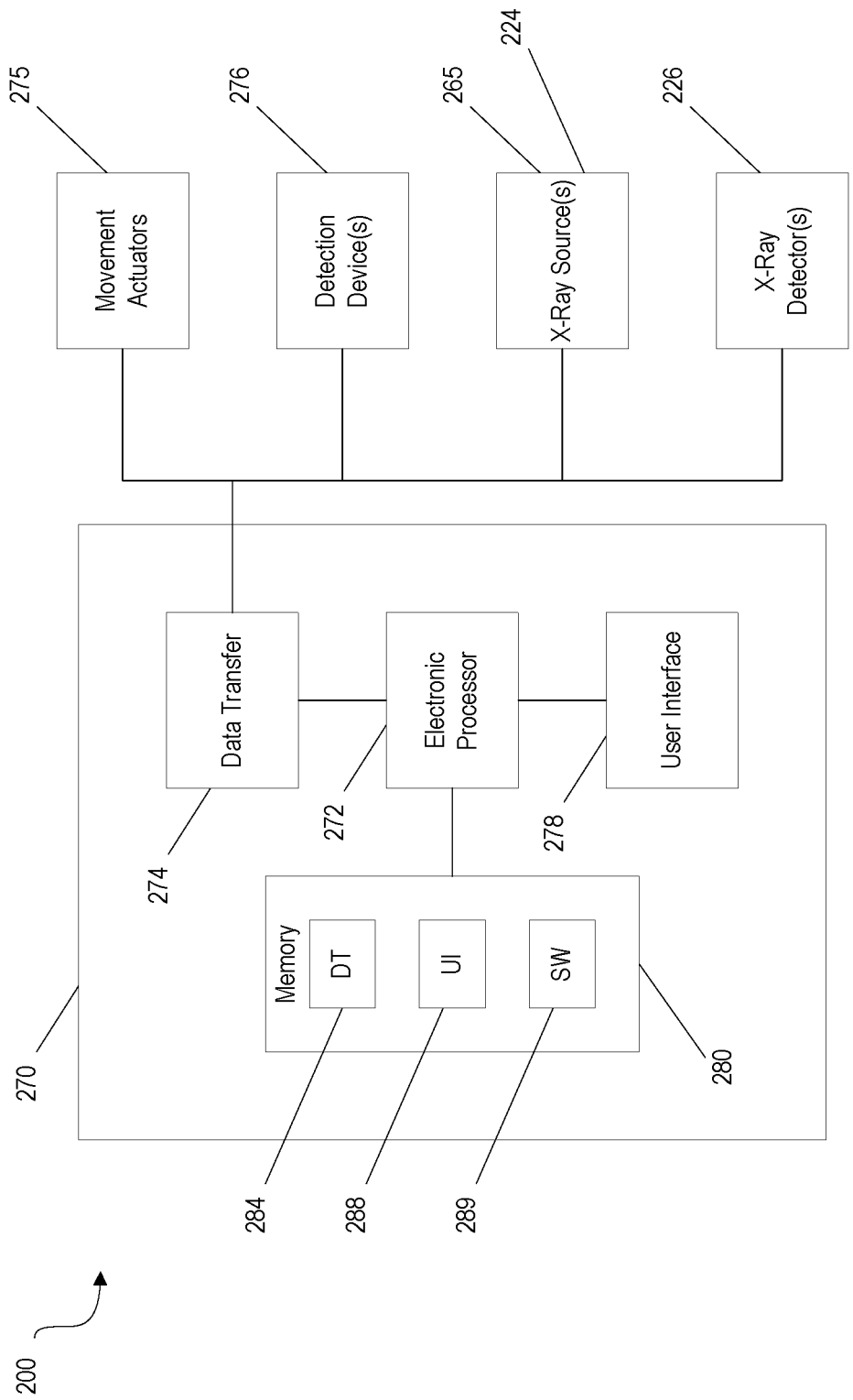
FIG. 1E is a block diagram of a control system for the X-ray imaging system of FIG. 1A.
Figure 1F:
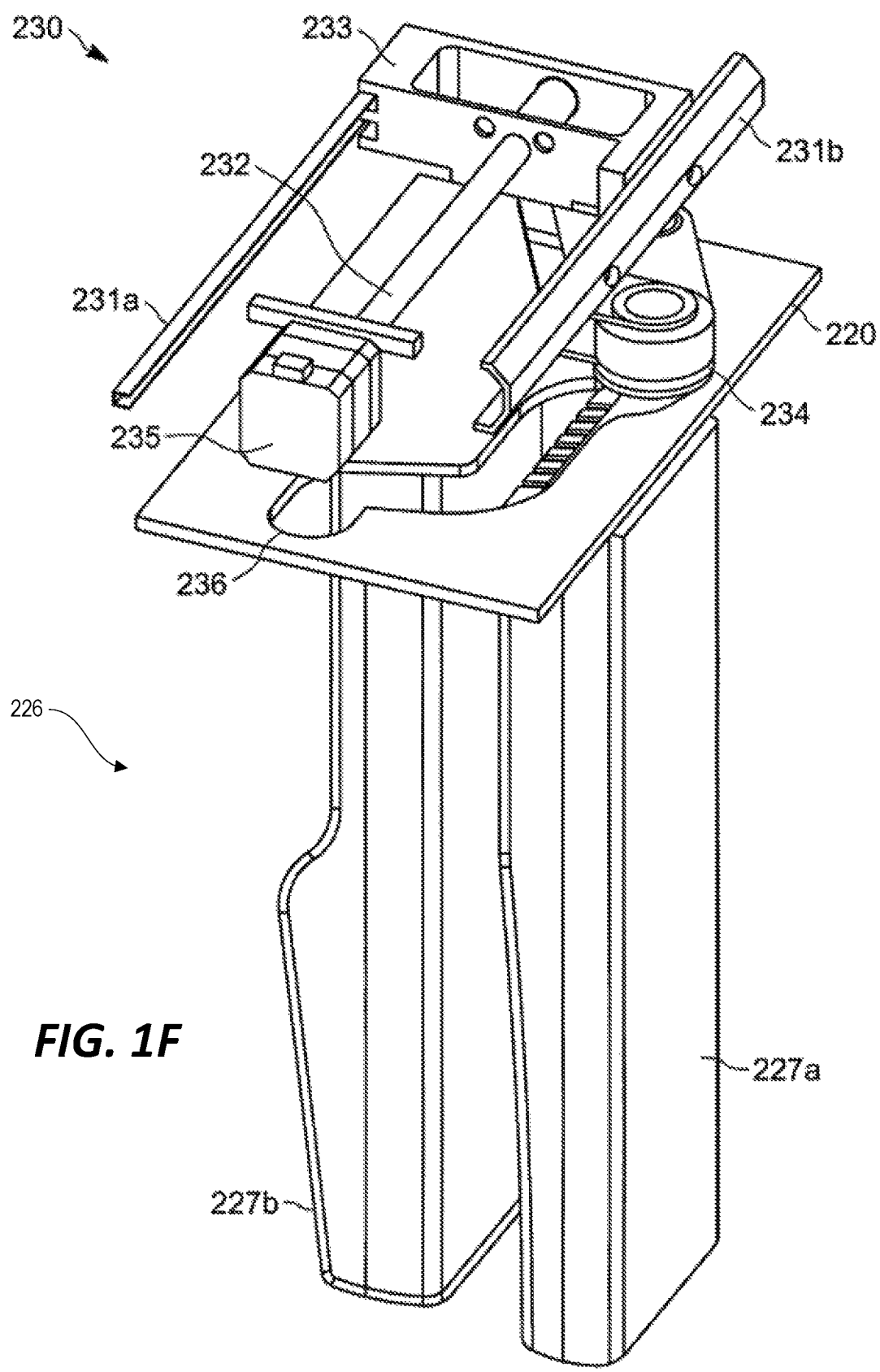
FIG. 1F illustrates an exemplary embodiment of a two detector X-ray imaging unit, exemplarily configured in a Panoramic imaging position.

On the other end of the rotating part 220 is the X-ray imaging detector unit 226, which can include, for example, one or two X-ray detectors 227a, 227b (see FIG. 1F). An example embodiment of a one-detector X-ray imaging detector unit 226 can include one X-ray detector 227 which may include one Panoramic detector, one Cephalometric detector, which also enables Panoramic imaging, one Panoramic/CT combination detector, one Panoramic/CT/Cephalometric combination detector, or one detector configured to be used in Panoramic/CT imaging and in one-shot Cephalometric imaging.

The one-detector X-ray imaging detector unit 226 can be adjustable, for example, by rotating the X-ray imaging detector unit 226 relative to the rotating part 220 so that one detector of the X-ray imaging detector unit 226 can be positioned preferably perpendicularly to the used first X-ray source 224 or second X-ray source 265 (described in further detail herein) and/or by moving one detector of the X-ray imaging detector unit 226 in a linear fashion relative to the rotating part 220 for adjusting a distance between the one detector or X-ray imaging detector unit 226 and the first X-ray source 224 in Panoramic/CT imaging.

In an example of a two-detector X-ray detector unit 226, the detector unit 226 can include one Panoramic detector and one CT detector, or one Cephalometric detector, which also enables Panoramic imaging. In a two-detector embodiment of the detector unit 226, the detectors are arranged, for example, successively in Panoramic imaging, whereupon the Panoramic or Cephalometric detector is arranged as a front detector for arranging magnification ratio for the imaging mode, and the CT detector as a rear detector. The swap of the detectors 227a, 227b (see FIG. 1F) is arranged so that the front detector 227a moves aside by means of moving means 230, for example, a rail 231a, 231b and a rotator configured to move along the rail 231a, 231b and to rotate so that the front detector 227a slides, for example, next to a rear detector 227b, when it is necessary to use the rear detector 227a in CT imaging or the front detector 227a in Cephalometric imaging. Alternatively, the front detector 227a can be moved to another position relative to the rear detector 227b in Cephalometric imaging. The place of the front detector 227a in Cephalometric imaging may depend upon on how the front detector 227a is displaced by means of the swap movement, and the R- and L-movements relative to the X-ray source 265 that is used. The Cephalometric detector 227a can be positioned preferably perpendicularly to the used X-ray source 265. The front detector 227a returns similarly by sliding, when it is necessary to move the front detector 227a back to the front position.

The rotating part 220 can include a detector motor 235 configured to move at least one detector by means of the moving means 230, if the detector unit 226 includes separate detectors 227a, 227b for the Panoramic and CT imaging.

The system 200 includes the column 240 for adapting a height Z of the system 200—and the rotating part 220. The column 240 includes height adapting means 241 which may include, for example, a height motor, a gear, and a threaded rod, and telescopic or counter weighted means configured to be driven by the height motor, for providing an up/down movement Z to adapt the height of the rotating part 220 to the height of the patient 201 for the Panoramic, Cephalometric, or CT imaging modes. The height adapting means 241 can realize the Z-movement, for example, as a movement of the height adapting means and/or as a telescopic or counterweighted movement.

A lower shelf or second patient support 242 is attached to the column 240. The lower shelf or second patient support 242 is used for positioning a patient 201 for imaging, for example, Panoramic and/or CT imaging and for supporting the patient 201, for example, from a tip of the patient's 201 chin by a chin support CS during the imaging. In some cases, the system 200 may only include one patient support, for example, the lower shelf or second patient support 242.

Alternatively, when the system 200 includes a seated patient's 201 positioning system (not shown), the Z-movement is realized, for example, by adapting in the Z-direction the height of at least one of the following: a chair, the lower shelf 242, and the column 240.

The lower shelf 242 can also include a head support (not shown), which supports, for example, the patient's 201 forehead and/or temple in the Panoramic/CT imaging position.

The system 200 includes the upper shelf 250, which supports the rotating part 220. In one example, the upper shelf 250 is attached to an upper end of the column 240 with a pivoting joint (means) 252, which enables a pivot movement P of the upper shelf 250 around the column 240 and in respect to a lower shelf 242 so that the rotating part 220 is over, for example, the lower shelf 242.

The upper shelf 250 includes pivot movement means 253, which includes, for example, a pivot motor 253 configured to pivot the upper shelf 250 around the column 240 by means of the pivoting joint 252.

The upper shelf 250 includes linear movement means 223, for example, a linear conveyor configured to support the rotation means of the rotating part 220 and to enable the rotating part 220 to rotate around the rotation axis 222, at least one rail and/or track configured to guide the linear conveyor in the upper shelf 250, and a linear motor configured to drive the linear conveyor along the at least one rail and the upper shelf 250, which enable the rotating part 220 and the rotation means to move with respect to the upper shelf 250 by means of a linear movement L. The linear movement means 223 of the upper shelf 250 can be provided so that L movement in a plane of the upper shelf 250 is a direct linear movement, for example, it is parallel to the upper shelf 250 or it is in a certain angle with respect to the parallel direction, or the L-movement in the plane of the upper shelf 250 is a non-direct linear movement having for example a curved path or a devious path.

The rotation means attach the rotating part 220 to the upper shelf 250. The rotation means are able to move with at least one L-movement so that the axis 222 and, thus, the rotation center in respect to the upper shelf 250 can be adjusted along the L-movement. Thus, the axis 222 can be positioned within a plane defined by the P-movement of the upper shelf 250 and the L-movement of the rotating part 220 during the imaging. By using a rotating P-movement, rather than a linear X-movement, to adjust the lateral position of the rotating part 220, it is possible to design a lighter and thinner upper shelf 250, thus giving the system 200 a smaller footprint.

In addition, the system 200 may include on one side of the column 240 a first Cephalometric arm 260 that has a certain first length. The arm 260 attaches a Cephalometric patient support 262 to the system 200 at a certain first distance that corresponds with the first length from the column 240. However, in other embodiments, the system 200 might not include a first Cephalometric arm 260 and, instead, provides a Cephalometric patent support positioned by other mechanism (e.g., fixedly coupled to the column without the use of an arm).

The Cephalometric patient support 262, which has a significantly simpler structure than in traditional Cephalometric units, includes Cephalometric patient support means 268, 269, for example, two adjustable ear rods 268 and an adjustable nasion support 269, for supporting the patient 201 to be imaged. The patient's head is supported, for example from an outer part of the ear canal with the ear buds 268A (shown in FIG. 1D) included in the ear rods 268 and from the nasion support 269 placed in contact with the top of the nasal bridge. The adjustable ear rods 268 and adjustable nasion support 269 is attached to the Cephalometric patient support 262 in a manner that enables them to rotate, for example, two main imaging positions: lateral and PA projections. The lateral projection is basically a side view and the PA projection is from back to front view of a skull of the patient.

The ear rods 268 can be tiltable or rotatable ear rods having a down position, where the ear rods 268 support the patient 201, and an up position, where it is possible to place the patient in the Cephalometric imaging position or where the patient can depart from the Cephalometric imaging position, when the tilted or rotated ear rods 268 in the up position provide a clear passage of the patient. Although the example of FIG. 1A includes a Cephalometric patient support 262 for positioning the head of a patient for Cephalometric imaging, other implementations may include other types of patient support for other types of imaging. For example, the system 200 may be configured to include a patient hand support for positioning the hand of a patient for carpus imaging.

In addition, the system 200 may include on other side of the column 240 a second Cephalometric arm 261 that has a certain second length. Attached to the second Cephalometric arm 261 is a second X-ray source 265, which is used in Cephalometric imaging. The second Cephalometric arm holds the second x-ray source at a second distance from the system 200, corresponding to a second length from the column 240. The X-ray source 265 includes an X-ray beam limiting device 267 for the Cephalometric imaging. Optionally, the X-ray beam limiting device 267 can be attached to the X-ray source 265. The X-ray source 265 can be configured to rotate around a rotation axis 264 by means of rotation means 264A configured to perform a scanning movement S. The axis 264 of the X-ray source 265 is in line with a focal spot of the X-ray source 265 so that it passes through the focal spot. The arm 261 or the X-ray source 265 includes a rotating motor, which is configured to rotate the X-ray source 265 around the axis 264, which coincides with the focal spot of the X-ray source 265.

As noted, in some embodiments, the arms 260, 261 can be separate arms attached to the column 240, or it is possible to use one arm 260, 261, which includes the Cephalometric head 262 in its one end and the X-ray source 265 with the X-ray beam limiting device 267 in the other end of the single arm 260, 261.

In addition, the rotating part 220 can include a Cephalometric (secondary) collimator 266, which is used in the Cephalometric imaging together with one detector of the detector unit 226. The Cephalometric collimator 266 is attached, for example, to one (right) side of the rotating part 220 (for example, X-ray source 224), as depicted in FIG. 1C. Alternatively, the Cephalometric collimator can be attached, for example, to another (left) side of the rotating part 220 (for example, X-ray source 224).

In addition, the rotating part 220 can include a detector motor 235 configured to rotate at least one detector of the detector unit 226 for the Cephalometric imaging, and a collimator motor configured to adjust a position (height) of the Cephalometric collimator 266 in the Z-direction and/or a position of the collimator of the X-ray source 224. Alternatively, or in addition, the X-ray beam limiting motor or the collimator motor can be configured to adjust both the X-ray beam limiting device 228 and the Cephalometric collimator 266.

The rotating part 220 is driven over the Cephalometric patient support 262, for example, with the P-, R-, and L-movements, so that the detector unit 226 and the Cephalometric collimator 266 are positioned for Cephalometric imaging.

The X-ray source 265 can be configured to provide, together with, for example, the detector unit 226 (for example, the Cephalometric detector 227a attached to the detector unit 226) and the Cephalometric collimator 266 in the rotating part 220, a Cephalometric image from the positioned patient 201, when it is rotated around the axis 264 by means of the S-movement, and the detector unit 226 and the Cephalometric collimator 266 are arranged to move, for example, by means of at least one of the P-, R-, and L-movements of the rotating part 220. Alternatively, the scanning movement of the X-ray beam—for example, a linear S-movement can be performed by moving the X-ray beam limiting device 267 of the X-ray source 265.

If the one-shot detector is used, the detector unit 226 and the Cephalometric collimator 266 are positioned by means of at least one of the P-, R-, and L-movements, but the image can be taken without these movements and/or without the S-movement.

In some implementations, the arms 260, 261 can be arranged so that a height of the Cephalometric patient support 262 with the ear rods 268 and nasion support 269 is fixed relative to the X-ray source 265. However, the fixed height may cause problems, because an anatomy of patients 201 varies for example, the vertical distance where ear openings are located compared to patient's 201 shoulders differs significantly from one patient 201 to another. Thus, either the patient 201 is located too low in the resultant Cephalometric image, showing only upper vertebras, or the patient 201 is located so high in the images that the shoulder of the patient 201 touches the detector unit 226, which is a problem especially with a scanning. Furthermore, the preferred Cephalometric imaging geometry requires that the focal spot and the tips of the ear rods 268 are at the same (horizontal) axis. In to reduce these problems, variable length ear rods 268 can be used while keeping the arms 260, 261 fixed height relative to each other.

Alternatively or in addition, in order to eliminate these problems, the X-ray imaging system 200 can include Cephalometric height adjusting means (not shown) that are configured to independently adjust the height—in respect to the column 240—of the arms 260, 261 that support the Cephalometric head 262 at the one end and the X-ray source 265 on the other end.

When the operator has adjusted the height of the arms 260, 261 by means of an up/down $Z_c$-movement, the focal spot follows the tips of the ear rods 268 automatically and, thus, the geometry (ear rod tip to focal spot line) remains intact. Yet, the detector unit 226 and the Cephalometric collimator 266 on each side of the patient 201 take their height from the column 240 and, thus, are on a different height in respect to the ear rods 268 and the patient 201 than before the adjustment.

The Cephalometric height adjusting means provides a way to adapt an exposed area to a given anatomy of the patient 201 by enabling an operator (user) to adjust the height of the patient 201 without compromising the geometry.

Since the first and second X-ray sources 224, 265 can be arranged at different heights with respect to the column 240 in the Z direction by means of the height adapting means 241 and/or the Cephalometric height adjusting means, it is possible to position the patient 201 without any additional adjustment of the Cephalometric head 262 in the Z direction as it is needed when using the X-ray source 224 of the rotating part 220 for the Cephalometric imaging. The detector unit 226 and the secondary collimator 266 are positioned for imaging using L-movement, P-movement, and/or R-movement.

In addition, by using the P-movement, the structure of the X-ray imaging system 200 is made simpler and cheaper, because the Cephalometric imaging can optionally be implemented by using only one "non-detachable" detector unit 226. This reduces the risk of breaking the detector unit 226 because there is no need to remove it from a holder of the rotating part 220 to detach it from a holder of the Cephalometric head 262 when changing the imaging mode from the Panoramic/CT mode to the Cephalometric mode. The detector for Panoramic imaging in the detector unit 226 can be rotated from the Panoramic imaging position to the Cephalometric imaging position so that it is possible to use the same detector in both Panoramic and Cephalometric imaging.

In addition, the structure of the X-ray imaging system 200 provides a simple workflow when, for example, the change from the Panoramic/CT mode to the Cephalometric mode—the movement of the rotating part 220 from the Panoramic/CT imaging position to the Cephalometric position without changing the detector unit 226 from one holder to other holder—is automated, thus decreasing both the amount of manual work required and the time needed for the work flow.

It is also possible that the X-ray imaging system 200 includes the upper shelf 250 that pivots around the column 240 and the rotating part 220 that is configured to be positioned by means of the above-described L-, P-, and/or R-movements for providing the Panoramic and/or CT imaging, but has a more conventional Cephalometric head 262 comprising the Cephalometric detector, the secondary collimator, and the patient positioning support parts.

Cephalometric imaging is provided by means of the X-ray source 224 of the rotating part 220, and the secondary collimator and the Cephalometric detector of the Cephalometric head 262. The X-ray source 224 is arranged to scan the patient's 201 head with the R-, L-, and/or P-movements. The X-ray beam is collimated by the secondary collimator and captured by the Cephalometric detector, which are synchronized with the X-ray beam.

FIG. 1B illustrates a positioning of the x-ray imaging system 200 for Panoramic/CT imaging. A patient 201 will be positioned with their head supported by placing the chin of the patient 201 on the lower shelf 242 and possibly to the head support of the system 200 in a Panoramic/CT imaging position, where the rotating part 220 is over the lower shelf 242.

If the upper shelf 250 as well as the rotating part 220 are in a different position than the Panoramic/CT imaging position—in a Cephalometric imaging position or in an intermediate position between, for example, the Panoramic/CT and Cephalometric imaging positions—the upper shelf 250 is moved from that position to the Panoramic/CT imaging position by the P-movement and, then, the rotating part 220 is further adjusted by the R- and L-movements so that the rotating part 220 is ready for the Panoramic/CT imaging. In implementations that include one or more other additional patient supports (e.g., a hand support for carpus imaging), the system 200 may be further configured to position the rotating part 220 proximate to each additional patient support for imaging using R-, L- and/or P-movements.

In addition, the rotating part 220 can have a patient positioning position, where the X-ray source 224 or the detector unit 226 are out of the way and do not interfere with the positioning of the patient 201 to the Panoramic/CT and/or Cephalometric imaging positions when the rotating part 220 is over the lower shelf 242 or the Cephalometric head 262. The patient positioning position can be accomplished by the R-movement so that the rotating part 220 is rotated to such position, where it is possible to place the patient 201 to the Panoramic/CT and/or Cephalometric imaging positions or to remove the patient 201 by moving the patient's 201 head between the X-ray source 224 and the detector unit 226. Alternatively, it is possible to realize the patient positioning position by means of the P-movement and/or the L-movement, whereupon the whole rotating part 220 is moved away from the Panoramic/CT and/or Cephalometric imaging positions, when the patient 201 is positioned.

The positioned X-ray source 224 and the detector unit 226 are configured to provide a Panoramic image when the rotation axis 222—a rotation center of the rotating part 220—is positioned by at least one of the P- and L-movements. In some implementations, the system is configured to perform Panoramic imaging by adjusting the P-, L-, and/or R-movements to control the position of the x-ray source 224 and the detector unit 226 before or during image capture scanning.

Depending on the sensor technology used, the image can be clocked out using a TDI mode or a full frame read-out mode of the detector. In the TDI mode, the image is read out one column at a time, whereas in the full frame mode, the image is read out whole image frame at a time. The Panoramic (sharp) layer is defined by the velocities of the movements and, in the case of TDI, the readout rate of the Panoramic detector. When using a full frame detector, the final shape of the layer is calculated on the computer after the scan. Rotation angle is, for example, about 270 degrees, but this is not intended to be limiting.

During CT imaging, the patient 201 is also supported by the lower shelf 242 and possibly by the head support of the X-ray imaging system 200 in the Panoramic/CT imaging position. The X-ray source 224 and the detector unit 226 are configured to provide a CT image when the detector unit 226 is attached to the rotating unit and the rotation center of the rotating part 220 is positioned so that it can coincide with the ROI.

The positioned X-ray source 224 and the detector unit 226 are configured to provide a CT image, for example, CBCT image, when the detector unit 226 is attached to the rotating part 220, and the rotation axis 222 is positioned by at least one of the R-, L-, and P-movements during the CT imaging.

When the X-ray imaging system 200 is used with a symmetric imaging geometry, CT imaging can be carried out by using only the R-movement and reading out the CT detector in a full frame mode. Alternatively, or in addition, CT imaging can be carried out by using the P-, R-, and L-movements, using the controlling arrangement in the upper shelf 250, for positioning the virtual rotation axis of the rotating part 220 so that it coincides with the ROI. Thus, projection X-ray images of the ROI are produced in a way that the center of the ROI and the R-movement coincide. In one embodiment, the effective rotation angle (aperture) ranges, for example, from approximately 180 to 360 degrees depending on the X-ray imaging system 200.

When the system 200 is used in an offset imaging, CT imaging can be carried out by scanning the image by using the R-, L-, and P-movement. By driving these R-, L-, and P-movements in synchronism, the effective center of the rotation can be deflected to the side of the X-ray beam and, thus creating an offset geometry. Offset scanning can be provided by a first "solid" offset geometry and a full 360 degree rotation of the CT detector.

Alternatively, the offset scanning can be provided by a second offset geometry, where the patient 201 is imaged by scanning an essentially maximal first imaging offset with approximately 180 degree rotation of the detector in a first imaging direction. Then, the detector is displaced to the other side of the rotation center to obtain an essentially maximal second imaging offset by approximately 180 degree rotation of the detector in a second imaging direction, which is opposite to the first direction. Alternatively, the detector is rotated to the starting position, displaced to the other side of the rotation center, and, then, scanning the essentially maximal second imaging offset by approximately 180 degree rotation in the first direction.

Alternatively, offset scanning can be provided by a third offset geometry, where the patient 201 is imaged by a first imaging offset, where the edge of the X-ray beam area touches the rotation center, and by 360 degree rotation of the detector. Next, the detector and the X-ray source 224 are displaced parallel in such a way that the X-ray beam area moves away from the rotation center so it hits or slightly overlaps the previously imaged area. Then, the detector is rotated 360 degrees for completing a second imaging offset.

The system 200 provides same versatility in the CT imaging geometry by means of the R-, L-, and P-movements instead of the R-, L-, X-, and N-movements required in imaging and patient positioning by some conventional systems.

FIG. 1C illustrates a positioning of the patient 201 and the x-ray system 200 during Cephalometric imaging. In the Cephalometric imaging position, where the rotating part 220 is over the patient support means 268, 269 located at the Cephalometric head 262, the patient 201 is supported to the patient support means 268, 269.

If the upper shelf 250 as well as the rotating part 220 are in a different position than the Cephalometric imaging position, for example, in a Panoramic/CT imaging position or in an intermediate position between the Panoramic/CT and Cephalometric imaging positions—the upper shelf 250 is moved from that position to the Cephalometric imaging position by the P-movement, and then the rotating part 220 is further adjusted by the R- and L-movements so that the rotating part 220 is ready for the Cephalometric imaging.

The positioned X-ray source 265 is configured to scan the supported patient 201 by means of the X-ray beam limiting device 267 attached to the X-ray source 265 and by means of the S-movement. The detector unit 226—and the rotating part 220—is configured to move synchronously with the X-ray source 265 by at least two of the R-, L-, and P-movements during the Cephalometric imaging.

The X-ray beam from the X-ray source 265 is arranged to scan the patient's 201 head by rotating the X-ray source 265 and the X-ray beam limiting device 267 with the S-movement around the axis 264. Alternatively, the S-movement can be performed by moving (for example, linearly) the X-ray beam limiting device 267. It is also possible that the S-movement is provided as a vertical scanning movement instead of the horizontal S-movement, if the detector of the detector unit 226 used in Cephalometric imaging is positioned horizontally. Alternatively, Cephalometric imaging can be performed without the S-movement if a sufficiently large detector (so-called, "one shot" detector) is used for the one-shot Cephalometric image.

The X-ray beam is then further collimated by the Cephalometric collimator 266 and finally captured by the synchronously moved Cephalometric or combination detector in the detector unit 226. The system 200 simplifies the movements during the Cephalometric imaging, because no additional movement means are needed for the Cephalometric collimator 266 and the detector of the detector unit 226.

As noted above, during Cephalometric imaging, the rotating part 220 is moved into position around the Cephalometric patient support 262 (e.g., with the X-ray source 224 and the detector unit 226 positioned on opposite sides of the Cephalometric patient support 262). FIG. 1D is a side view of a patient 201 positioned for Cephalometric imaging using the Cephalometric patient support 262. The patient 201 is positioned with the ear buds of the adjustable ear rod 268 positioned in each ear and with the adjustable nasion support 269 contacting the bridge of the nose of the patient 201. Although the nasion support 269 is shown in FIG. 1D as contacting the bridge of the nose, in some implementations, the adjustable nasion support 269 may be sized and positioned for the nose of the patient 201 to rest on top of the adjustable nasion support 269 during Cephalometric imaging.

FIG. 1E illustrates the functional elements (e.g., the control system) of the X-ray imaging system 200. The X-ray imaging system 200 includes a controller 270 that receives input from a control panel and that is configured to control the X-ray imaging system 200, and its above-described movements and imaging processes. The controller 270 is attached, for example, to the column 240. The controller 270 includes at least one processor 272 for performing user and/or software initiated instructions and for processing data, and at least one non-transitory computer-readable memory 280 for storing and maintaining data, for example, instructions, software, and data files. Although FIG. 1E shows only a single controller 270, in some implementations, the X-ray imaging system 200 is configured to include multiple different controllers to provide the functionality of the X-ray imaging system 200.

In addition, the controller 270 includes a data transfer portion 274 for sending control commands to one or more movement actuators 275, for example, the pivot, linear, height, rotating, detector, X-ray beam limiting, and collimator motors, drivers, or other means configured to provide the movements of the parts of the X-ray imaging system 200, and/or receiving data from measuring devices or other detection devices 276 configured to detect the function of parts of the X-ray imaging system 200.

In addition, the data transfer portion 274 is also configured to send control commands to the at least one of followings: at least one of X-ray source 224 and/or X-ray source 265, and the detector unit 226. The data transfer portion 274 is also configured to receive information from at least one of the following: the at least one X-ray source 224, 265, and the detector unit 226.

In addition, the controller 270 includes a user interface portion 278 which may include at least one of the following: at least one function key, a touchscreen, and a wired or wireless remote controller, for inputting control commands, and for receiving information and/or instructions.

The at least one memory 280 stores at least a data transfer application 284 for execution by the processor 272 controlling the data transfer portion 274, a user interface application 288 for execution by the processor 272 for controlling the user interface portion, and a computer program (code) 289 for controlling the function of the system 200, for example, at least the movement devices 275, detection devices 276, the at least one X-ray source 224, 265, and the detector unit 226. In addition, execution of the computer program 289 can control, for example, imaging parameters, imaging sizes, and imaging modes.

The at least one memory 280 and the computer program 289 are configured to, with the at least one processor 272, cause the system 200 at least to provide actions described in context of FIGS. 1A-1D, for example, to control positions of the detector unit 226 and the Cephalometric collimator 266 by at least one or two of the R-, L-, and P-movements.

The computer program 289 can be a computer program product that includes a tangible, non-volatile (non-statutory) computer-readable medium bearing a computer program 289 embodied therein for use with a computer (controller 270).

FIG. 1F illustrates one example of a detector unit 226 that includes two detectors 227a, 227b, which can provide a Panoramic, CT, and Cephalometric image. The rotating part 220 includes moving means 230, which move the at least one detector 227a, 227b relative to the rotating part 220 for positioning the at least one detector 227a, 227b for the imaging, and the detector motor 235 configured to drive the moving means 230. The detector 227a can be, for example, a Panoramic detector, which is configured to provide the Panoramic image, or a Cephalometric detector, which is configured to provide a Cephalometric image and a Panoramic image. The CT detector 227b is configured to provide a CT image. The moving means 230 can comprise, for example, at least one of rails 231a, 231b, a threaded rod 232, a conveyor unit 233, a guide unit 234 that is connected to the conveyor unit 233 and attaches the detector 227a to the rotating part 220, and a guide groove 236. The detector motor 235 moves the detector 227a by means of the threaded rod 232, which moves the conveyor unit 233 along the rails 231a, 231b so that the guide unit 234 guides the detector 227a along the guide groove 236. The guide groove 236 illustrated in the example of FIG. 1F is only one example and, in other implementations, the guide groove 236 can be provided in other shapes and configurations including a groove that is, for example, direct, curved, devious, or combinations thereof.

FIG. 1F illustrates one example of a Panoramic imaging position, wherein the X-ray source 224 and the Panoramic or Cephalometric detector 227a, which is attached to the rotating part 220, can provide the Panoramic image. The detector 227a and the CT detector 227b are arranged successively in the Panoramic imaging position so that the detector 227a is between the X-ray source 224, 265 and the CT detector 227b—the detector 227a is in front of the CT detector 227b relative to the X-ray source 224, 265. To capture CT image data, the detector motor 235 operates the moving means 230 to move the detector 227a along the guide groove 236 until the guide unit 234 is positioned at the opposite end of the guide groove 236 and the detector 227a is no longer positioned between the CT detector 227b and the x-ray source 224. In some embodiments, the CT imaging position can also be a Cephalometric imaging position, wherein the X-ray source 265 can provide together with the Cephalometric detector 227a, which is attached to the rotating part 220, the Cephalometric image.

As discussed above, in some embodiments, the first X-ray source 224 and the combination detector 227, which is attached to the rotating part 220, are used for providing the Panoramic image and the CT 30 image. The second X-ray source 265 and the combination detector 227, which is attached to the rotating part 220, are used for providing the Cephalometric image. The combination detector 227 can be driven similarly as the detector 227a in the detector unit 226 illustrated in FIG. 1F by for example, similar moving means 230, but not necessary by all its movements.

The Panoramic image is taken when the combination detector 227 has been driven to the Panoramic imaging position similarly as illustrated in FIG. 1F, whereupon the combination detector 227 is in a front position. The CT and Cephalometric images are taken when the combination detector 227 has been driven to the CT/Cephalometric imaging position whereupon the combination detector 227 is in a back position. In addition, the combination detector 227 can be positioned by means of the moving means 230 and by means of at least one of the R-, L-, and P-movements. Alternatively, the combination detector 227 can be positioned by means of at least one of the R-, L-, and P-movements. So, the combination detector 227 can be moved between at least of two of the Panoramic, CT, and Cephalometric imaging positions by means of the moving means 230 and/or by means of at least one of the R-, L-, and P-movements.

In order for the system 200 to be able to properly perform Cephalometric imaging in the position/configuration shown in FIG. 1C, the system 200 must be able to determine, for example, a position of the patient's head relative to the detector unit 226 and/or the Cephalometric x-ray source 265. In some implementations, the position of the patient's head can be inferred based on a position of the Cephalometric patient support 262. However, the position of the Cephalometric patient support 262 may not be precisely known by the imaging system 200. As discussed above, the first arm 260 and the second arm 261 of the Cephalometric imaging system are installed after the components for Panoramic and CT imaging are installed and calibrated. For example, the first arm 260 and the second arm 261 may be added to the system 200 as "add-ons" or accessories and, therefore, are not calibrated at the time of manufacture of the system 200. Additionally, in some implementations, the position of the first arm 260, the ear rod 268, and/or the nasion support 269 can be manually adjusted based for a particular patient 201.

In these and other situations, the system 200 must be calibrated, for example, to determine a position of the Cephalometric patient support 262 in a three-dimensional coordinate space used by the system 200. Additionally, in some implementations, the appropriate relative angles and positions of the Cephalometric x-ray source 265 and the secondary collimator 266 are determined relative to the position of the patient's head. The position of the Cephalometric patient support 262 and/or the appropriate relative angles and positions of the Cephalometric x-ray source 265 and the secondary collimator 266 can be determined, for example, by performing one or more calibration "sweeps." A calibration sweep is performed by controllably adjusting a position of one or more component of the system 200 while emitting x-rays (e.g., from the first x-ray source 224 or the Cephalometric x-ray source 265) and while capturing image data through the detector unit 226.

In some implementations, a calibration phantom is used in the calibration process. The calibration phantom can be permanently or selectively affixed to the Cephalometric patient support 262. FIG. 2A illustrates a first example of a calibration phantom 281 that is selectively affixed to the Cephalometric patient support 262 at a position equidistant between the ear rods 268. As discussed below, this calibration phantom 281 can be detected in the image data captured during the calibration process and used to determine a position of the Cephalometric patient support at least in the horizontal (x, y) plane.

Figure 2B:
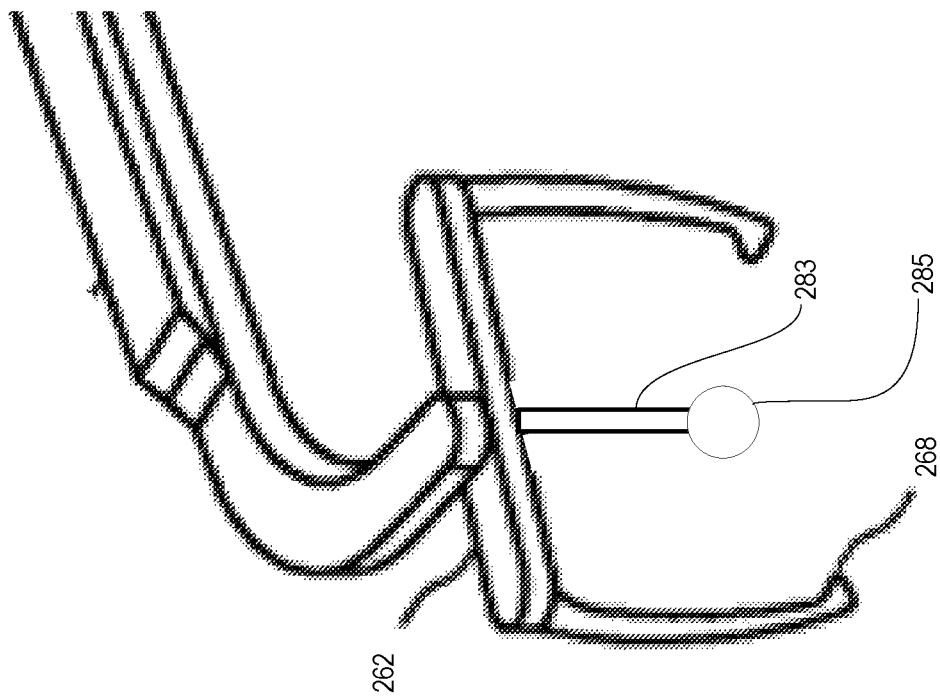
FIG. 2B is a perspective view of the Cephalometric patient support with a second example of a calibration phantom for calibration of the x-ray imaging system for Cephalometric imaging.
Figure 2A:
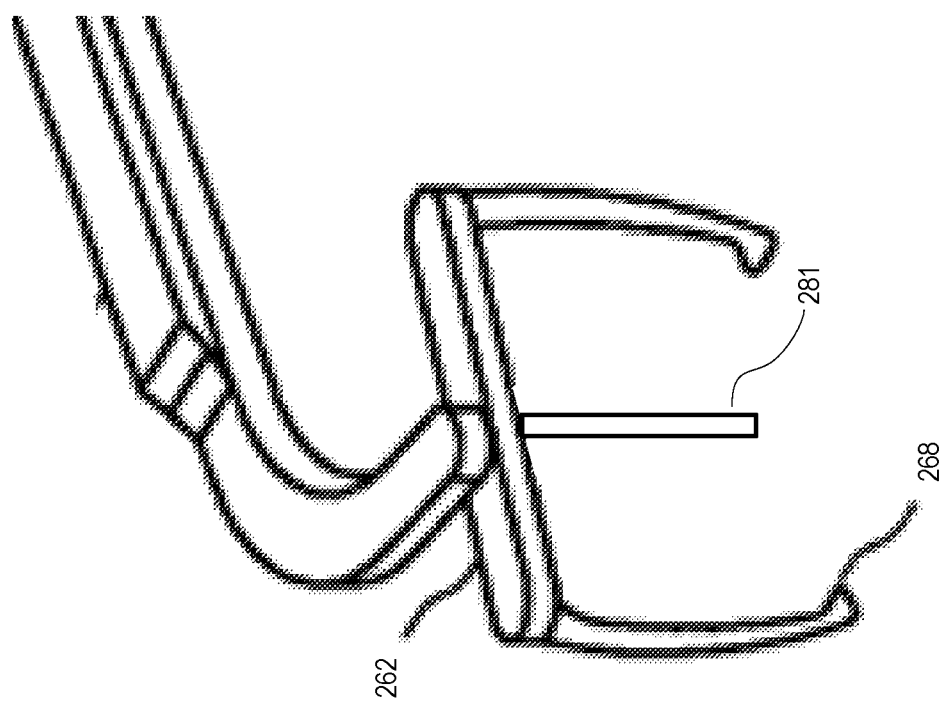
FIG. 2A is a perspective view of a Cephalometric patient support with a first example of a calibration phantom for calibration of the x-ray imaging system for Cephalometric imaging.

FIG. 2B illustrates another example of a calibration phantom 283 that is selectively affixed to the Cephalometric patient support. The calibration phantom 283 of FIG. 2B includes a spherical body 285 coupled to a distal end of the linear rod. Because the actual size and dimensions of the spherical body 285 are known, the calibration phantom 283 can be used, for example, to determine a distance between the x-ray detector and the calibration phantom 283 (and, by extension, the Cephalometric patient support 262).

Figure 2D:
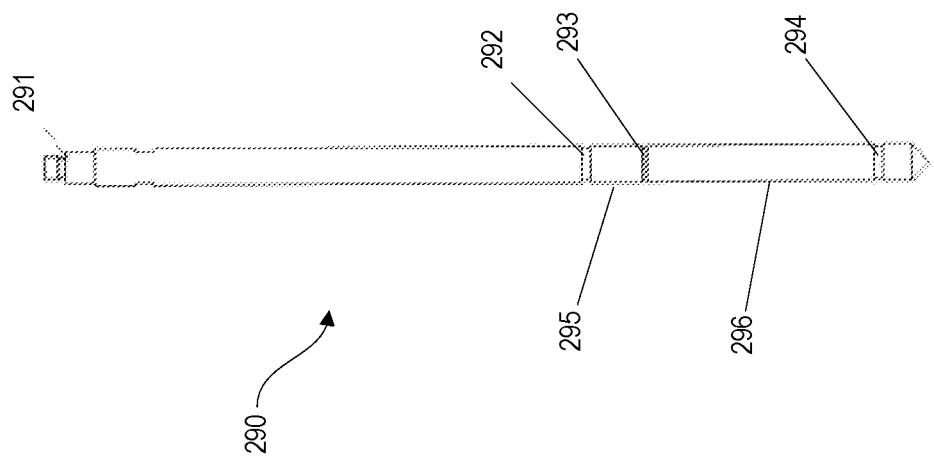
FIG. 2D is an elevation view of a fourth example of a calibration phantom for calibration of the x-ray imaging system for Cephalometric imaging.
Figure 2C:
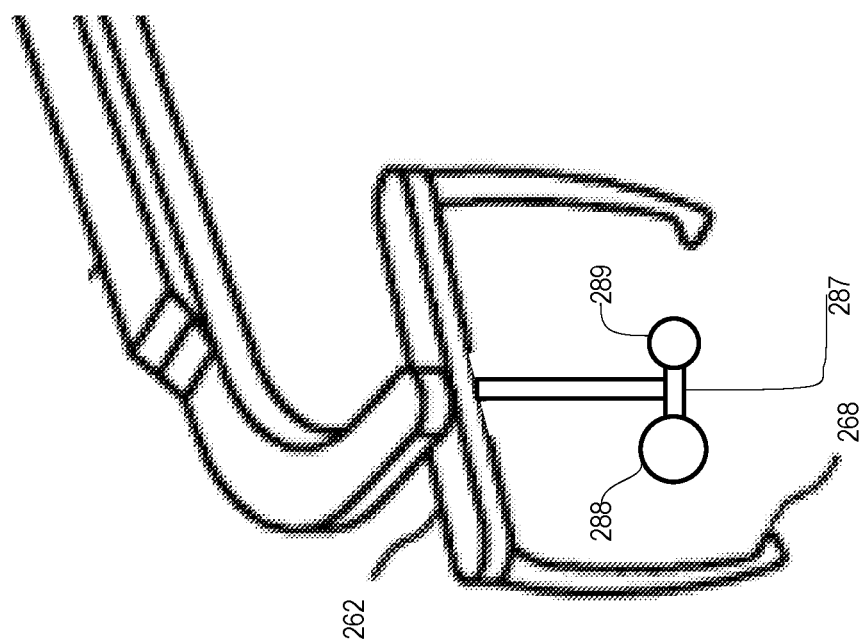
FIG. 2C is a perspective view of the Cephalometric patient support with a third example of a calibration phantom for calibration of the x-ray imaging system for Cephalometric imaging.

FIG. 2C illustrates yet another example of a calibration phantom 287 that is provided in the form of an inverted "T" and coupled to the Cephalometric patient support 262. The calibration phantom 287 includes two spherical bodies 288, 289 attached to the ends of the horizontal portion of the calibration phantom 287. In this example, the spherical bodies 288, 289 are provided with different diameters and the diameters of spherical bodies 288, 289 are known. Accordingly, as discussed in further detail below, a distance between the x-ray detector unit 226 and each spherical body 288, 289 of the calibration phantom 287 can be determined based on an apparent magnification of the spherical bodies in captured image data.

FIG. 2D illustrates still another example of a calibration phantom 290. The calibration phantom 290 includes a linear body with a coupling notch 291 formed at a first end that selectively engages with a corresponding coupling on the Cephalometric patient support 262 in order to selectively couple and de-couple the calibration phantom 262 to a position on the Cephalometric patient support 262 (e.g., extending vertically downward from the Cephalometric patient support 262 as shown in FIG. 2A with respect to calibration phantom 281). The calibration phantom 290 also includes a plurality of grooves 292, 293, 294 formed around the circumference of the linear body of the calibration phantom 290 at different locations along the length of the calibration phantom 290. In some implementations, the grooves can be formed on the calibration phantom 290 with different widths—for example, the first groove 292 in the example of FIG. 2D is wider than the second groove 293. Similarly, the grooves can be positioned along the length of the calibration phantom 290 to provide, for example, different lengths of the linear body of the calibration phantom 290 between different grooves pairs. For example, in the calibration phantom 290 illustrated in the example of FIG. 2D, a section 295 of the linear body between the first groove 292 and the second groove 293 is shorter than a section 296 of the linear body between the second groove 293 and the third groove 294. Although the example illustrated in FIG. 2D includes three grooves, in other implementations, the calibration phantom 290 can be formed with more or fewer grooves. For example, in some implementations, the calibration phantom may be formed to include only one groove.

Figure 3A:
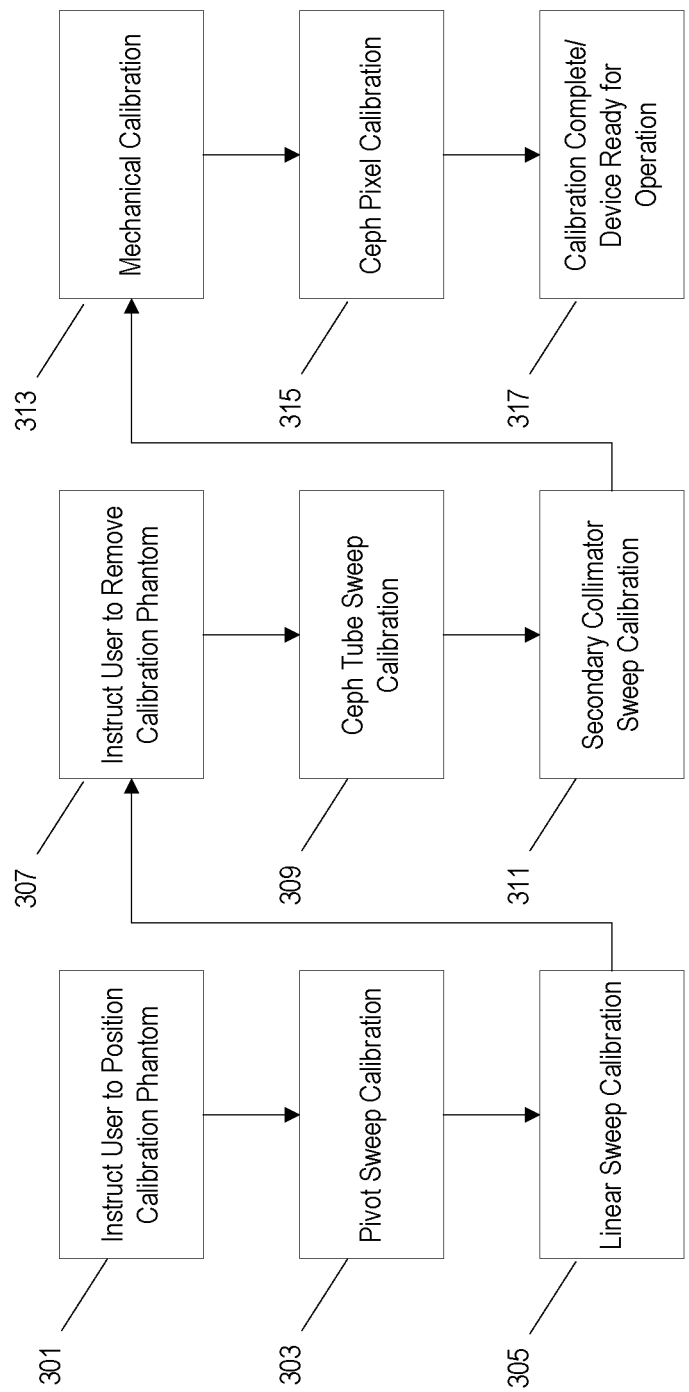
FIG. 3A is a flow chart of a method for calibrating an X-ray imaging system in accordance with some embodiments.

FIG. 3A illustrates an example of a method for calibrating the X-ray imaging system 200. The calibration method of FIG. 3A utilizes the calibration phantom 281 of FIG. 2A a stick mounted to the ear rods rotation axis at the Cephalometric patient support 262 (e.g., extending vertically downward midway between the ear buds). In the example of FIG. 3A, the X-ray imaging system 200 is configured to display on the user interface, upon initiation of the calibration process, an instruction to place the calibration phantom on the middle axis of the Cephalometric patient support 262 (step 301). Because the position of the x-ray source 224 and the detector unit 226 are controlled based on a known coordinate system, the X-ray imaging system 200 can determine the position of the Cephalometric patient support 262 in the same known coordinate system by performing one or more imaging scans. In the example of FIG. 3A, the X-ray imaging system 200 determines the middle point of the Cephalometric patient support 262 by performing two different scans. First, the X-ray imaging system 200 performs a "pivot sweep calibration" (step 303) by adjusting the pivot of the upper shelf 250 (e.g., P-rotation) in order to a scan the space containing the Cephalometric patient support 262 in a first direction. The X-ray imaging system 200 then performs a "linear sweep calibration" (step 305) in order to scan the space in a second direction. As described in further detail below, based on these two calibration scans, the X-ray imaging system 200 is able to determine a middle point of the Cephalometric patient support 262 in the x-y plane in the known coordinate system of the X-ray imaging system 200.

After determining the middle position of the Cephalometric patient support 262, the user is instructed to remove the calibration phantom (step 307) and the system performs a "Cephalometric tube sweep calibration" (step 309) in order to determine a "middle angle" position of the Cephalometric x-ray source 265 relative to the Cephalometric patient support 262. The system also performs a "secondary collimator sweep calibration" (step 311) to determine an appropriate position/orientation of the secondary collimator 266 relative to the Cephalometric x-ray source 265. In some implementations, the system may also apply one or more mechanical calibration steps (step 313) and/or a pixel calibration (step 315) before using the calibrated system to perform Cephalometric imaging.

FIG. 3B illustrates one example of a pivot sweep calibration 303 in further detail. After the calibration phantom is positioned on the Cephalometric patient support 262, the system 200 operates the pivot actuator to pivot the upper shelf 250 to a nominal Cephalometric imaging position (step 321). Because the pivoting movement of the upper shelf 250 and the rotating part 220 have already been calibrated (e.g., during manufacture), the system 200 is aware of the position of the first x-ray source 224 and the detector unit 226 in the known coordinate system. The rotating part 220 is rotated to a position where the upper shelf 250 can be pivoted without interfering with or contacting the Cephalometric patient support 262 (e.g., positioned with the detector unit 226 and first x-ray source 224 in line with the upper shelf 250). The first x-ray source 224 is then activated to irradiate the calibration phantom 281 (step 323) and the system operates the pivot rotation (p-rotation) to scan the space occupied by the Cephalometric patient support 262 (step 325). As the pivoting of the upper shelf 250 causes movement of the first x-ray source 224 and the detector unit 226, image data is captured by the detector unit 226 (step 327). After the pivot scan is complete, the image data is analyzed to determine a center of the calibration phantom 281 (step 329).

FIG. 3C illustrates one example of a linear sweep calibration 305 in further detail. After completing the pivot sweep calibration 303, the rotating part 220 is rotated approximately 90-degrees (step 331) so that a line between the first x-ray source 224 and the detector unit 226 is perpendicular to a length of the upper shelf (e.g., a line extending radially from the pivot axis). In this way, the rotating part 220 is able to move linearly along the length of the upper shelf 250 without contacting the Cephalometric patient support 262. The system 200 activates the first x-ray source 224 to irradiate the calibration phantom 281 (step 333) and operates a linear movement actuator to move the rotating part 220 in a linear direction along the length of the upper shelf 250 (step 335). As the linear movement of the rotating part 220 causes movement of the first x-ray source 224 and the detector unit 226, image data is captured by the detector unit 226 (step 337). After the linear sweep scan is complete, the image data is analyzed to determine a center of the calibration phantom 281 (step 339).

By determining the middle point of the calibration phantom 281 while performing both the linear sweep and the pivot sweep, the system 200 is now able to determine a location of a center point of the Cephalometric patient support in the x-y plane of the known coordinate system. In some implementations, the system 200 is configured to utilize a separate alignment procedure to properly align the Cephalometric patient support 262 in the vertical (Z) direction.

As described above in reference to FIG. 3A, after the system 200 has determined the position of the Cephalometric patient support 262 in the known coordinate system of the imaging system 200, the calibration phantom 281 can be removed. The system 200 then determines appropriate positioning of other system components relative to the Cephalometric patient support 262.

Figure 3D:
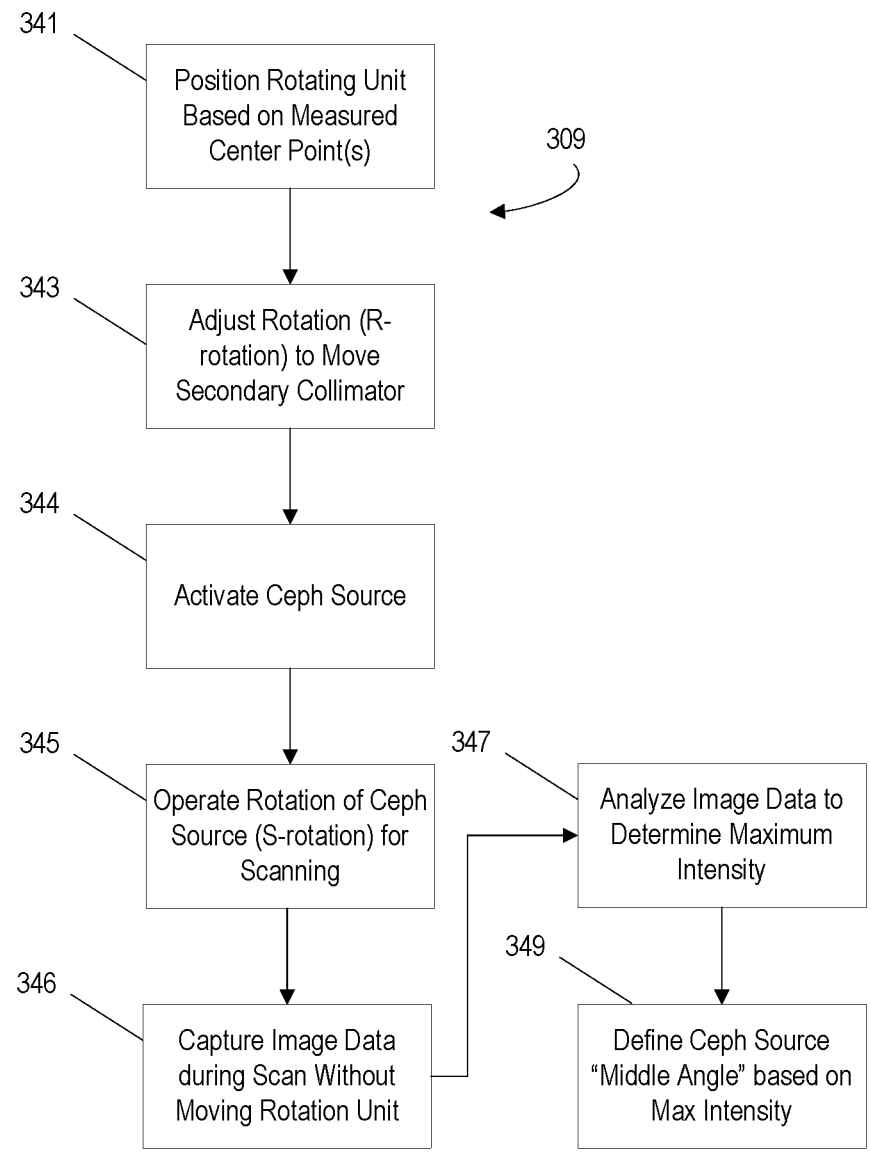
FIG. 3D is a flow chart of one example of a Cephalometric tube sweep calibration for use in the method of FIG. 3A.

As discussed above, in performing Cephalometric imaging, the system 200 will rotate the Cephalometric x-ray source 265 (S-rotation in FIG. 1A) while making corresponding adjustments to the position of the detector unit 226. However, in order to perform this type of scan, a position and orientation of the Cephalometric x-ray source 265 relative to the Cephalometric patient support 262 must be determined. FIG. 3D illustrates an example of a Cephalometric tube sweep calibration 309 that can be used by the system 200 to determine a middle angle of the Cephalometric x-ray source 265 relative to the Cephalometric patient support 262. The detector unit 226 is moved into position by adjusting the pivot of the upper shelf 250 (P-rotation), a linear position of the rotating part 220 along the length of the upper shelf 250, and a rotation of the rotating part 220 (R-rotation) (step 341). Additionally, in some implementations, the rotational position of the rotating part 220 and the position of the detector unit 226 are adjusted so that the x-ray beam from the Cephalometric x-ray source 265 does not pass through the secondary collimator before contacting the detector unit 226 (step 343). For example, as illustrated in FIG. 1F, the linear position of the detector 227a that is used for capturing image data during panoramic and Cephalometric imaging can be moved to an appropriate position along the guide groove 236 for calibration while the P-, L-, and/or R-movements are adjusted to position the detector 227a relative to the previously determined center point of the Cephalometric patient support 262.

After the detector unit 226 is positioned based on the previously determined center points of the Cephalometric patient support 262 and the secondary collimator 266 is moved out of the way, the Cephalometric x-ray source 265 is activated (step 344) and the Cephalometric x-ray source 265 is controllably rotated for scanning (step 345). Image data is captured by the detector unit 226 while the rotating unit 220 (and, therefore, the detector unit 226 and the secondary collimator 266) remains stationary (step 346). The captured data is then analyzed, for example, to determine the angular position of the Cephalometric x-ray source 265 that results in the maximum image intensity (step 347). In some examples, this angular position is then used to define a "middle angle" of the Cephalometric x-ray source 265 to guide movement of the Cephalometric x-ray source 265 (e.g., S-rotation) during Cephalometric imaging (step 349). In other implementations, for example, angular positions of the Cephalometric x-ray source 265 corresponding to the edges of the captured image data are determined and the "middle angle" of the Cephalometric x-ray source is determined based on a middle point between the detected edges of the image data.

Although the examples described above in reference to FIGS. 3A, 3B, and 3C refer to the use of the calibration phantom 281 as illustrated in FIG. 2A, the pivot sweep calibration of FIG. 3A and the linear sweep calibration of FIG. 3B can be performed using other types of calibration phantoms—for example, the calibration phantom 290 of FIG. 2D.

Figure 3E:
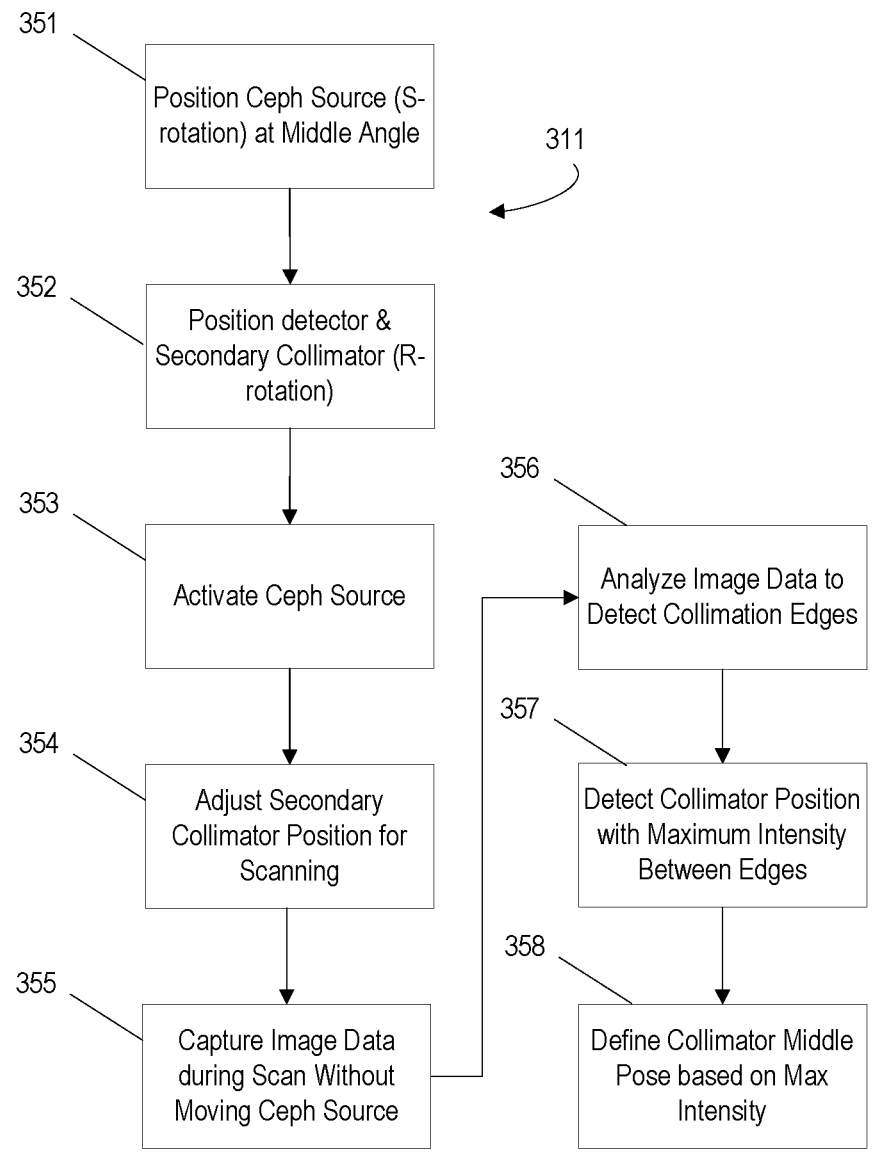
FIG. 3E is a flow chart of one example of a secondary collimator calibration for use in the method of FIG. 3A.

After the position/location of the Cephalometric patient support 262 is determined relative to the x-ray detector and the position of the Cephalometric x-ray source 265 is calibrated relative to the Cephalometric patient support 262, the X-ray imaging system 200, in the example of FIG. 3A, then performs a "secondary collimator sweep calibration" 311 to calibrate the positioning of the secondary collimator between the Cephalometric x-ray source 265 and the detector unit 226. FIG. 3E illustrates one example of a secondary collimator sweep calibration 311 that can be used to calibrate the position and orientation of the secondary collimator 266 for Cephalometric imaging. First, the Cephalometric x-ray source 265 is returned to the middle angle as determined in the "ceph tube sweep calibration" 309 (step 351). The rotating part 220 is then controllably rotated to position the detector unit 226 relative to the Cephalometric patient support 262 and to position the secondary collimator 266 between the Cephalometric x-ray source 265 and the detector unit 226 (step 352). The Cephalometric x-ray source 265 is then activated (step 353) and the position of the secondary collimator 266 is controllably adjusted for scanning (step 354). While the position and angle of the secondary collimator 266 are controllably adjusted, the detector unit 226 captures image data (step 355) and the Cephalometric x-ray source 265 remains stationary. The captured image data is then analyzed, for example, to detect collimation edges (step 356) and to detect a collimator position that results in a maximum intensity between the detected collimation edges (step 357). In some examples, a "middle pose" of the secondary collimator 266 is then defined based on the position that is determined to result in the maximum intensity (step 358).

After the X-ray imaging system 200 is calibrated to determine a position/location of the Cephalometric patient support 262 relative to the x-ray detector and to determine "middle positions" for both the Cephalometric x-ray source 265 and the secondary collimator 266, Cephalometric imaging can be performed by capturing image data while controllably coordinating the movements of the Cephalometric x-ray source 265, the secondary collimator 266, and the detector unit 226 (see, e.g., step 317 in FIG. 3A). However, in some implementations, additional calibration procedures may be performed before operating the X-ray imaging system 200 for Cephalometric imaging. For example, in FIG. 3A a mechanical calibration 313 and a pixel calibration 315 are performed.

In some implementations, the mechanical calibration 313 may be performed to align the ear rods 268 of the Cephalometric patient support 262 so that they overlap at the image plane at the ear rod rotation axis. This can be achieved, for example, by exposing a lateral Cephalometric image and displaying instructions on the user interface 278 instructing the user to make particular mechanical adjustments to the Cephalometric patient support 262.

Furthermore, in some implementations, the pixel calibration 315 can be used to calibrate pixel response and/or to find dead pixels in the detector unit 226 in order to create a "blemish map." This can be achieved, for example, by positioning the rotating part 220, the secondary collimator 266, and the Cephalometric x-ray source 265 in the "middle position" (e.g., where image intensity is the strongest). Image data is then captured by the detector unit 226 while all system components remain stationary. The captured image data is then analyzed to detect any dead pixels and to calibrate for pixel response.

In the method of FIG. 3A, the center position of the Cephalometric patient support 262 is determined by performing both a pivot sweep scan and a linear sweep scan while a calibration phantom is irradiated using the first x-ray source 224 coupled to the rotating part 220. However, in other implementations, the X-ray imaging system 200 may be configured to determine the center position of the Cephalometric patient support 262 using one or more other "sweeps." Also, in other implementations, the X-ray imaging system 200 may be configured to irradiate the calibration phantom using the Cephalometric x-ray source 265.

Figure 4:
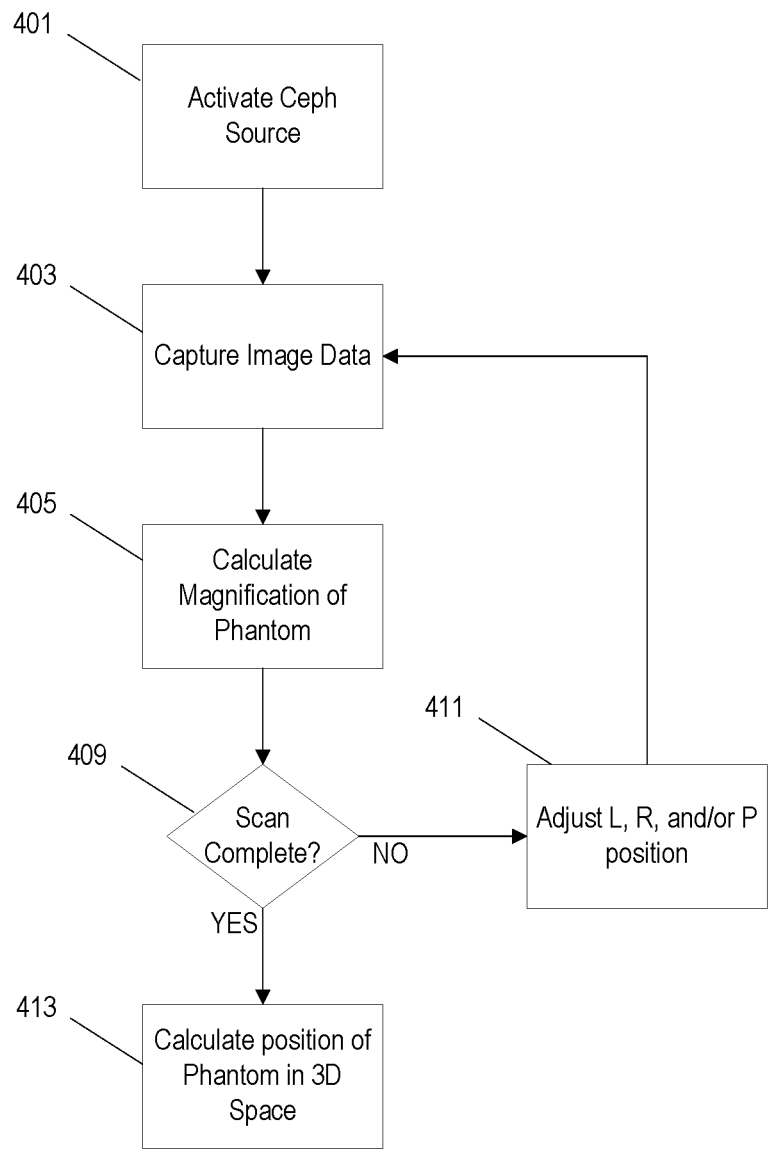
FIG. 4 is a flow chart of another example of a single sweep calibration for determining a position of the Cephalometric patient support.

FIG. 4 illustrates an example of an alternative calibration method for determining a position of the Cephalometric patient support 262. In this example, a calibration phantom that includes a body of known size and dimensions—for example, the known dimensions of the spherical bodies 288, 289 of the calibration phantom 287 in FIG. 2C, the known width of the grooves 292, 293, 294 of the calibration phantom 290 in FIG. 2D, and/or the known length and width of the sections 295, 296 between the grooves 292, 293, 294 of the calibration phantom 290 in FIG. 2D—is affixed to the Cephalometric patient support 262. Once the calibration phantom (for example, the calibration phantom 287 or the calibration phantom 290) is attached, the system 200 begins the calibration routine by activating the Cephalometric x-ray source 265 to irradiate the calibration phantom 287/290 (step 401). Image data is captured by the detector unit 226 (e.g., the combined detector illustrated in FIG. 1F) (step 403). The captured image data is analyzed and, based on a known size and known dimensions of the calibration phantom 287/290 and the apparent size/dimensions of the calibration phantom 287/290 in the captured image data, a magnification of the calibration phantom 287/290 is determined (step 405). The system 200 then adjusts a position of the detector relative to the calibration phantom 287/290 using a combination of L-, R-, and P-movements (step 411) until the scan is complete (step 409). The position of the calibration phantom 287/290 in the coordinate space for the system 200 is then calculated based on the determined magnification of the calibration phantom 287/290 in image data captured at each of a plurality of known positions of the detector unit 226 (step 413).

When using a calibration phantom with multiple bodies of known size/dimension, the system 200 may be configured to separately determine a magnification of the each body in image data. For example, in the image data captured at each of the plurality of known detector positions while using the calibration phantom 287 of FIG. 2C, the system 200 may be configured to detect both spherical bodies 288, 289 in the image data and to then calculate a relative magnification of each of the two spherical bodies 288, 289. Similarly, in the image data captured at each of the plurality of known detector positions while using the calibration phantom 290 of FIG. 2D, the system 200 may be configured to calculate a relative magnification of each of the grooves 292, 293, 294 and/or each sections 295, 296 between the grooves. Based on the magnification ratio of the two spherical bodies 288, 289, the grooves 292, 293, 294, and/or the sections 295, 296 at each of a plurality of different detector positions, the system 200 determines a distance between the detector unit 226 and the calibration phantom 287/290 at each of the detector positions. Based on this collection of determined distances and the known position/orientation of the detector unit 226 corresponding to each determined distance, the system 200 then determines a location of the calibration phantom 287/290 in the coordinate space of the system 200. Additionally, in some examples, the system 200 might also be configured to determine a position of the Cephalometric x-ray source 265 based on the magnification of the calibration phantom 287/290 in the image data (e.g., using the principle of source-object-distance (SOD)).

Although, FIG. 4 describes the adjustment of the L-, R-, and/or P-position of the system 200 as a discrete iterative step (step 411) performed after capturing data, in some implementations, movement of the detector unit 226 by L-, R-, and/or P-movements is performed as a continuous sweep and image data is captured by the detector unit 226 at different times/positions during continuous movement. Accordingly, the calibration method illustrated in FIG. 4 can be performed as a single "sweep" calibration. Furthermore, the path of the detector unit 226 during the sweep calibration of FIG. 4 can be defined and/or adjusted in various different examples based, for example, on the size, position, and dimensions of the imaging system 200, the patient support for which the system 200 is being calibrated, and/or the calibration phantom used in the calibration.

Finally, in some implementations, the system may be configured to utilize the additional calibration steps (including, for example, those illustrated in FIGS. 3D and 3E) to determine a middle angle of the Cephalometric x-ray source 265 and/or the secondary collimator 266 after determining the position of the Cephalometric patient support 262 using the method of FIG. 4 (or another calibration method).

The examples described above are only some of the possible calibration techniques that can be used for a combination CT, panoramic, and/or Cephalometric imaging system. In various implementations, some or all of the calibrations illustrated in FIG. 3A may be performed. Other implementations may include additional or alternative calibrations.

Some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

Embodiments and examples have been explained above with reference to the aforesaid embodiments and the several advantages have been demonstrated. It is clear that the invention is not restricted to these embodiments, but includes other embodiments and the following claims.

What is claimed is:

1. A method of operating an imaging system to perform Cephalometric imaging, the imaging system including:
   a column,
   an upper shelf coupled to the column,
   a rotating part coupled to the upper shelf and linearly translatable along a length of the upper shelf in a direction radial to the column,
   a first x-ray source coupled to the rotating part, and
   an x-ray detector coupled to the rotating part on an opposite side of a first imaging volume from the first x-ray source,
the method comprising:
   performing at least one calibration sweep by controllably adjusting a position of the x-ray detector relative to a Cephalometric patient support;
   capturing image data by the x-ray detector while performing the at least one calibration sweep; and
   determining a center position of the Cephalometric patient support relative to the imaging system in at least two dimensions based on the image data captured while performing the at least one calibration sweep.

2. The method of claim 1, further comprising performing Cephalometric imaging by operating a second x-ray source to emit x-rays towards a head of a patient and controllably adjusting a position of the x-ray detector on an opposite side of the head of the patient from the second x-ray source based on the determined center position of the Cephalometric patient support.

3. The method of claim 1, further comprising selectively coupling a Cephalometric support arm to the column, wherein the Cephalometric patient support is coupled to a distal end of the Cephalometric support arm.

4. The method of claim 3, further comprising selectively:
   coupling a Cephalometric x-ray source arm to the column, wherein a second x-ray source is rotatably coupled to a distal end of the Cephalometric x-ray source arm; and
   performing Cephalometric imaging by:
      positioning the x-ray detector based on the determined center position of the Cephalometric patient support, and
      operating the second x-ray source to emit x-rays towards the x-ray detector while scanning by controllably adjusting a rotation angle of the second x-ray source relative to the Cephalometric x-ray source arm.

5. The method of claim 1, further comprising:
   positioning the x-ray detector opposite a second x-ray source based on the determined center position of the Cephalometric patient support;
   operating the second x-ray source to project x-rays towards the x-ray detector while scanning by controllably adjusting a rotation angle of the second x-ray source; and
   determining a middle angle of the second x-ray source relative to the Cephalometric patient support by identifying, from image data captured by the x-ray detector while scanning with the second x-ray source, a rotation angle of the second x-ray source corresponding to a maximum intensity in the image data captured by the x-ray detector.

6. The method of claim 5, further comprising:
   controllably adjusting a position of the rotating part to position a collimator coupled to the rotating part outside of an imaging volume between the second x-ray source and the x-ray detector prior to capturing the image data used to determine the middle angle of the second x-ray source; and
   capturing the image data used to determine the middle angle of the second x-ray source relative to the Cephalometric patient support while the collimator is positioned outside of the imaging volume between the second x-ray source and the x-ray detector.

7. The method of claim 6, further comprising:
   controllably adjusting a position of the rotating part to position the collimator coupled to the rotating part inside the imaging volume between the second x-ray source and the x-ray detector;
   controllably adjusting an orientation of the collimator while operating the second x-ray source to emit x-rays, while capturing image data by the x-ray detector, and while the rotation angle of the second x-ray source and the position of the x-ray detector remain stationary; and
   determining a middle pose of the collimator by:
      detecting collimation edges in the image data captured by the x-ray detector while controllably adjusting the orientation of the collimator, and
      identifying a collimator pose corresponding to a maximum image intensity within the collimation edges.

8. The method of claim 7, further comprising performing Cephalometric imaging by:
   positioning the collimator coupled to the rotating part inside the imaging volume between the second x-ray source and the x-ray detector so that x-rays emitted by the second x-ray source are collimated before reaching the x-ray detector, scanning with the second x-ray source by controllably adjusting the rotation angle of the second x-ray source based on the determined middle angle while emitting x-rays from the second x-ray source, and coordinating movements of the x-ray detector and the collimator with movements of the second x-ray source while scanning based at least in part on the determined center position of the Cephalometric patient support and the determined middle pose of the collimator.

9. The method of claim 1, wherein the upper shelf is pivotably coupled to the column, and wherein performing the at least one calibration sweep includes:

performing a pivot sweep calibration by controllably adjusting a pivot angle of the upper shelf while emitting x-rays from the first x-ray source; and performing a linear sweep calibration by controllably adjusting a linear position of the rotating part along the upper shelf while emitting x-rays from the first x-ray source.

10. The method of claim 9, further comprising coupling a calibration phantom to the Cephalometric patient support, wherein the calibration phantom includes a linear body positioned vertically from the center position of the Cephalometric patient support, and wherein determining the center position of the Cephalometric patient support includes identifying a location of the calibration phantom in image data captured during the pivot sweep calibration and in image data captured during the linear sweep calibration.

11. The method of claim 1, wherein performing the at least one calibration sweep includes controllably adjusting at least two selected from a group consisting of a pivot angle of the upper shelf relative to the column, a linear position of the rotating part along the upper shelf, and a rotational angle of the rotating part relative to the upper shelf, the method further comprising:

coupling a calibration phantom to the Cephalometric patient support, the calibration phantom including at least one body of a known size and known dimensions; and irradiating the calibration phantom with x-rays from a second x-ray source coupled to the column while performing the at least one calibration sweep, and wherein determining the center position of the Cephalometric patient support relative to the imaging system includes:

determining a magnification of the at least one body of the calibration phantom at each of a plurality of detector positions of the x-ray detector, determining a distance between the x-ray detector and the calibration phantom at each of the plurality of detector positions of the x-ray detector based at least in part on the determined magnification, and determining the center position of the Cephalometric patient support relative to the imaging system based on the distance between the x-ray detector and the calibration phantom at each of the plurality of detector positions of the x-ray detector.

12. An imaging system comprising:
a column;
an upper shelf coupled to the column;
a rotating part coupled to the upper shelf and linearly translatable along a length of the upper shelf in a direction radial to the column;
a first x-ray source coupled to the rotating part;
an x-ray detector coupled to the rotating part on an opposite side of a first imaging volume from the first x-ray source; and a controller configured to:
perform at least one calibration sweep by controllably adjusting a position of the x-ray detector relative to a Cephalometric patient support, capture image data by the x-ray detector while performing the at least one calibration sweep, and determine a center position of the Cephalometric patient support relative to the imaging system in at least two dimensions based on the image data captured while performing the at least one calibration sweep.

13. The imaging system of claim 12, wherein the controller is further configured to perform Cephalometric imaging by operating a second x-ray source to emit x-rays towards a head of a patient and controllably adjusting a position of the x-ray detector on an opposite side of the head of the patient from the second x-ray source based on the determined center position of the Cephalometric patient support.

14. The imaging system of claim 12, further comprising:
a Cephalometric support arm selectively couplable to the column; and
wherein a distal end of the Cephalometric support arm is coupled to the Cephalometric patient support.

15. The imaging system of claim 14, further comprising:
a Cephalometric x-ray source arm selectively couplable to the column; and
a second x-ray source rotatably coupled to a distal end of the Cephalometric x-ray source arm,
wherein the controller is further configured to perform Cephalometric imaging by:
positioning the x-ray detector based on the determined center position of the Cephalometric patient support, and operating the second x-ray source to emit x-rays towards the x-ray detector while scanning by controllably adjusting a rotation angle of the second x-ray source relative to the Cephalometric x-ray source arm.

16. The imaging system of claim 12, further comprising a second x-ray source, wherein the controller is further configured to:

position the x-ray detector opposite a second x-ray source based on the determined center position of the Cephalometric patient support, operate the second x-ray source to project x-rays towards the x-ray detector while scanning by controllably adjusting a rotation angle of the second x-ray source, and determine a middle angle of the second x-ray source relative to the Cephalometric patient support by identifying, from image data captured by the x-ray detector while scanning with the second x-ray source, a rotation angle of the second x-ray source corresponding to a maximum intensity in the image data captured by the x-ray detector.

17. The imaging system of claim 12, wherein the upper shelf is pivotably coupled to the column, and wherein the controller is configured to perform the at least one calibration sweep by:

performing a pivot sweep calibration by controllably adjusting a pivot angle of the upper shelf while emitting x-rays from the first x-ray source, and performing a linear sweep calibration by controllably adjusting a linear position of the rotating part along the upper shelf while emitting x-rays from the first x-ray source.

18. The imaging system of claim 17, wherein the controller is configured to determine the center position of the Cephalometric patient support by identifying a location of a calibration phantom in image data captured during the pivot sweep calibration and in image data captured during the linear sweep calibration,
   wherein the calibration phantom includes a linear body selectively coupled to vertically to the center position of the Cephalometric patient support.

19. The imaging system of claim 12, further comprising a second x-ray source coupled to the column,
   wherein the controller is further configured to irradiate a calibration phantom with x-rays from the second x-ray source while performing the at least one calibration sweep, wherein the calibration phantom is selectively coupled to the Cephalometric patient support and includes at least one body of a known size and known dimensions,
   wherein the controller is configured to perform the at least one calibration sweep by controllably adjusting at least two selected from a group consisting of a pivot angle of the upper shelf relative to the column, a linear position of the rotating part along the upper shelf, and a rotational angle of the rotating part relative to the upper shelf, and
   wherein the controller is configured to determine the center position of the Cephalometric patient support relative to the imaging system by:
      determining a magnification of the at least one body of the calibration phantom at each of a plurality of detector positions of the x-ray detector,
      determining a distance between the x-ray detector and the calibration phantom at each of the plurality of detector positions of the x-ray detector based at least in part on the determined magnification, and
      determining the center position of the Cephalometric patient support relative to the imaging system based on the distance between the x-ray detector and the calibration phantom at each of the plurality of detector positions of the x-ray detector.

* * * * *